(12) United States Patent
Mulligan et al.

(10) Patent No.: US 12,708,514 B2
(45) Date of Patent: Aug. 18, 2026

(54) SYSTEMS AND METHODS FOR DELIVERING PROSTHETICS TO TREAT A CARDIAC VALVE

(71) Applicant: CroiValve Ltd., Dublin (IE)

(72) Inventors: Aoife Mulligan, Sandymount (IE); Gabriel Sobrino-Serrano, Kinvara (IE); Ian O'Gorman, Dublin (IE); Gavin Kenny, Doughiska (IE); Paul Heneghan, Raheny (IE); Conor Quinn, Malahide (IE); Pascal Launois, Dundrum (IE)

(73) Assignee: CroiValve Ltd., Dublin (IE)

( * ) Notice: Subject to any disclaimer, the term of this patent is extended or adjusted under 35 U.S.C. 154(b) by 393 days.

(21) Appl. No.: 18/291,565

(22) PCT Filed: Jul. 27, 2022

(86) PCT No.: PCT/IB2022/056960
§ 371 (c)(1),
(2) Date: Jan. 23, 2024

(87) PCT Pub. No.: WO2023/026113
PCT Pub. Date: Mar. 2, 2023

(65) Prior Publication Data

US 2024/0261101 A1 Aug. 8, 2024

Related U.S. Application Data

(60) Provisional application No. 63/226,683, filed on Jul. 28, 2021.

(51) Int. Cl.
*A61F 2/24* (2006.01)

(52) U.S. Cl.
CPC .......... *A61F 2/2463* (2013.01); *A61F 2/2466* (2013.01); *A61F 2220/0008* (2013.01); *A61F 2220/0025* (2013.01); *A61F 2250/006* (2013.01)

(58) Field of Classification Search
CPC .............. A61M 25/01; A61M 25/0054; A61M 2025/015; A61M 25/0136;
(Continued)

(56) References Cited

U.S. PATENT DOCUMENTS 2,684,069 A 7/1954 Shearman et al.
3,689,942 A 9/1972 Rapp
(Continued)

FOREIGN PATENT DOCUMENTS

AU 2016200392 B2 12/2017
CA 2705942 A1 5/2009
(Continued)

OTHER PUBLICATIONS

Berger et al., Comparison of results and complications of surgical and Amplatzer device closure of atrial septal defects, J. Thorac. Cardiovasc. Surg., 118(4):674-8 (1999).
(Continued)

*Primary Examiner* — Seema Mathew
(74) *Attorney, Agent, or Firm* — Greenberg Traurig, LLP; Christopher C. Bolten; Albert K. Heng

(57) ABSTRACT

Apparatus for repairing a cardiac valve, e.g., a tricuspid valve, are provided. The apparatus may include a prosthetic device coupled to an elongated support to suspend and maintain the prosthetic device within the cardiac valve. The support may include a proximal, delivery portion detachably coupled a distal, implantable portion coupled to the prosthetic device, and two or more adjustable bends to facilitate navigation through the patient's anatomy. The adjustable
(Continued)

bends may be selectively adjusted, components of the distal, implantable portion may be locked to each other, and the proximal, delivery portion may be detached from the distal, implantable portion responsive to actuation at a handle operatively coupled to the support. The prosthetic device may be formed of biocompatible material coupled to a frame, and may have prosthetic leaflets that allow blood flow in one direction during, e.g., diastole, but prevent blood regurgitation during, e.g., systole.

31 Claims, 28 Drawing Sheets

(58) Field of Classification Search
CPC ....... A61M 2025/0161; A61M 25/0041; A61F 2/2427; A61F 2/243; A61F 2/2439; A61F 2/2436; A61F 2/2433; A61F 2/9517; A61F 2/2466
See application file for complete search history.

(56) References Cited

U.S. PATENT DOCUMENTS 3,746,003 A 7/1973 Blake et al.
5,509,428 A 4/1996 Dunlop
5,792,179 A 8/1998 Sideris
6,168,614 B1 1/2001 Andersen et al.
6,332,893 B1 12/2001 Mortier et al.
6,461,366 B1 10/2002 Seguin
6,527,800 B1 3/2003 McGuckin, Jr. et al.
6,540,782 B1 4/2003 Snyders
6,582,462 B1 6/2003 Andersen et al.
6,629,534 B1 10/2003 St. Goar et al.
6,752,813 B2 6/2004 Goldfarb et al.
6,755,812 B2 * 6/2004 Peterson ........... A61M 25/0152 604/528
6,764,510 B2 7/2004 Vidlund et al.
6,821,297 B2 11/2004 Snyders
6,869,414 B2 * 3/2005 Simpson ........... A61M 25/0152 604/95.04
6,893,459 B1 5/2005 Macoviak
6,955,689 B2 10/2005 Ryan et al.
7,077,862 B2 7/2006 Vidlund et al.
7,542,808 B1 * 6/2009 Peterson ................ A61N 1/056 607/125
7,678,145 B2 3/2010 Vidlund et al.
7,704,277 B2 4/2010 Zakay et al.
7,785,366 B2 8/2010 Maurer et al.
7,854,762 B2 12/2010 Speziali et al.
7,901,454 B2 3/2011 Kapadia et al.
8,070,805 B2 12/2011 Vidlund et al.
8,216,302 B2 * 7/2012 Wilson .................... A61F 2/246 623/2.11
8,216,303 B2 7/2012 Navia
8,449,606 B2 5/2013 Eliasen et al.
8,460,370 B2 6/2013 Zakay et al.
8,470,028 B2 6/2013 Thornton et al.
8,475,525 B2 7/2013 Maisano et al.
8,480,730 B2 7/2013 Maurer et al.
8,486,136 B2 7/2013 Maurer et al.
8,506,624 B2 8/2013 Vidlund et al.
8,579,967 B2 11/2013 Webler et al.
8,758,432 B2 6/2014 Solem
8,888,844 B2 11/2014 Eliasen et al.
8,894,705 B2 11/2014 Eliasen et al.
8,923,973 B2 12/2014 Gross
8,932,348 B2 1/2015 Solem et al.
8,961,596 B2 2/2015 Maisano et al.
8,968,395 B2 3/2015 Hauser et al.
8,979,922 B2 3/2015 Jayasinghe et al.
8,992,605 B2 3/2015 Zakai et al.
9,005,279 B2 4/2015 Gabbay
9,011,523 B2 4/2015 Seguin
9,132,007 B2 9/2015 Menk et al.
9,161,837 B2 10/2015 Kapadia
9,232,998 B2 1/2016 Wilson et al.
9,232,999 B2 1/2016 Maurer et al.
9,289,297 B2 3/2016 Wilson et al.
9,358,112 B2 6/2016 Hlavka et al.
9,370,424 B2 6/2016 Call et al.
9,414,918 B2 8/2016 Chau et al.
9,474,605 B2 10/2016 Rowe et al.
9,492,634 B2 * 11/2016 Moehle ............... A61M 1/3661
9,498,330 B2 11/2016 Solem
9,510,946 B2 12/2016 Chau et al.
9,545,305 B2 1/2017 Wilson et al.
9,579,199 B2 2/2017 Hauser et al.
9,629,720 B2 4/2017 Nguyen et al.
9,636,223 B2 5/2017 Khalil et al.
9,763,782 B2 9/2017 Solem
9,827,101 B2 11/2017 Solem et al.
10,047,421 B2 8/2018 Khan et al.
10,300,286 B2 * 5/2019 Ward ................ A61N 1/37205
10,383,729 B2 8/2019 Quinn
10,682,231 B2 6/2020 Quinn
10,952,854 B2 3/2021 Heneghan et al.
10,987,220 B2 4/2021 Quinn
11,207,182 B2 12/2021 Heneghan et al.
11,219,525 B2 1/2022 Vesely et al.
11,364,365 B2 * 6/2022 Regnier ............... A61B 5/6861
11,565,081 B1 * 1/2023 Jones ................ A61M 25/0041
12,226,314 B2 * 2/2025 Reimer ................. A61F 2/2436
12,420,067 B2 * 9/2025 Balkovec ........ A61M 25/09041
12,543,943 B2 * 2/2026 Piskun ..................... A61B 1/32
2002/0103532 A1 8/2002 Langberg et al.
2003/0105520 A1 6/2003 Alferness et al.
2003/0109852 A1 * 6/2003 Peterson ........... A61M 25/0041 604/528
2003/0181855 A1 * 9/2003 Simpson ........... A61M 25/0041 604/95.04
2004/0059351 A1 3/2004 Eigler et al.
2004/0102830 A1 * 5/2004 Williams ............ A61N 1/0573 607/125
2004/0127981 A1 7/2004 Rahdert et al.
2004/0138744 A1 7/2004 Lashinski et al.
2004/0153146 A1 8/2004 Lashinski et al.
2004/0210307 A1 10/2004 Khairkhahan
2004/0225354 A1 11/2004 Allen et al.
2004/0243229 A1 12/2004 Vidlund et al.
2005/0033446 A1 2/2005 Deem et al.
2005/0075723 A1 4/2005 Schroeder et al.
2005/0107810 A1 5/2005 Morales et al.
2005/0107871 A1 5/2005 Realyvasquez et al.
2005/0187616 A1 8/2005 Realyvasquez
2005/0222488 A1 10/2005 Chang et al.
2005/0228495 A1 10/2005 Macoviak
2006/0058871 A1 3/2006 Zakay et al.
2006/0178700 A1 8/2006 Quinn
2006/0193899 A1 8/2006 Sawhney
2006/0241745 A1 10/2006 Solem
2007/0093890 A1 4/2007 Eliasen et al.
2007/0185571 A1 8/2007 Kapadia et al.
2007/0198082 A1 8/2007 Kapadia et al.
2007/0232992 A1 10/2007 Kutsko et al.
2007/0255399 A1 11/2007 Eliasen et al.
2007/0265700 A1 11/2007 Eliasen et al.
2008/0033541 A1 2/2008 Gelbart et al.
2008/0243245 A1 10/2008 Thambar et al.
2009/0076600 A1 3/2009 Quinn
2009/0149949 A1 6/2009 Quinn
2009/0240326 A1 9/2009 Wilson et al.
2009/0281618 A1 11/2009 Hill et al.
2010/0185276 A1 7/2010 Vidlund et al.
2010/0217382 A1 8/2010 Chau et al.
2010/0262233 A1 10/2010 He
2010/0298929 A1 11/2010 Thornton et al.
2010/0298930 A1 11/2010 Orlov
2011/0022004 A1 * 1/2011 Kipperman ....... A61M 25/0041 604/264
2011/0022164 A1 1/2011 Quinn et al.
2011/0060407 A1 3/2011 Ketai et al.
2011/0112632 A1 5/2011 Chau et al.

(56) References Cited

U.S. PATENT DOCUMENTS

2011/0224784 A1 9/2011 Quinn
2011/0257721 A1 10/2011 Tabor
2012/0010700 A1 1/2012 Spenser
2012/0046739 A1 2/2012 Von Oepen et al.
2012/0109079 A1* 5/2012 Asleson ................ A61F 2/2427 606/129
2012/0232563 A1* 9/2012 Williams .......... A61M 25/0108 606/129
2013/0018459 A1 1/2013 Maisano et al.
2013/0090728 A1 4/2013 Solem
2013/0172978 A1 7/2013 Vidlund et al.
2013/0310928 A1 11/2013 Morriss et al.
2013/0325110 A1 12/2013 Khalil et al.
2013/0338763 A1 12/2013 Rowe et al.
2014/0031928 A1 1/2014 Murphy et al.
2014/0039615 A1 2/2014 Padala et al.
2014/0135910 A1 5/2014 Hauser et al.
2014/0200657 A1 7/2014 Maurer et al.
2014/0207230 A1 7/2014 Wilson et al.
2014/0243968 A1 8/2014 Padala
2014/0257347 A1 9/2014 Eidenschink
2014/0276395 A1 9/2014 Wilson et al.
2014/0276971 A1 9/2014 Kovach
2014/0336751 A1 11/2014 Kramer
2014/0350662 A1 11/2014 Vaturi
2014/0379075 A1 12/2014 Maurer et al.
2015/0073547 A1 3/2015 Eliasen et al.
2015/0112429 A1 4/2015 Khairkhahan et al.
2015/0127097 A1 5/2015 Neumann et al.
2015/0134050 A1 5/2015 Solem et al.
2015/0202043 A1 7/2015 Zakai et al.
2015/0223934 A1 8/2015 Vidlund et al.
2015/0257884 A1 9/2015 Subramanian et al.
2015/0305861 A1 10/2015 Annest
2016/0030166 A1 2/2016 Kapadia
2016/0074164 A1 3/2016 Naor
2016/0081798 A1 3/2016 Kocaturk
2016/0089233 A1 3/2016 Lee et al.
2016/0089239 A1 3/2016 Hauser et al.
2016/0113762 A1 4/2016 Clague et al.
2016/0166380 A1 6/2016 Seguin et al.
2016/0166382 A1 6/2016 Nguyen
2016/0184098 A1 6/2016 Vaturi
2016/0193043 A1 7/2016 Kim
2016/0199181 A1 7/2016 Kramer
2016/0242909 A1 8/2016 Ketai et al.
2016/0262741 A1 9/2016 Gilmore et al.
2016/0262886 A1 9/2016 Wang
2016/0278920 A1 9/2016 Braido et al.
2016/0287387 A1 10/2016 Wei
2016/0317788 A1* 11/2016 Merkel ............. A61M 25/0068
2017/0035561 A1 2/2017 Rowe et al.
2017/0143478 A1 5/2017 Schwartz et al.
2017/0196687 A1 7/2017 Braido et al.
2017/0209265 A1 7/2017 Karapetian et al.
2017/0216575 A1* 8/2017 Asleson ................ A61N 1/056
2017/0224444 A1 8/2017 Viecilli et al.
2017/0224477 A1 8/2017 Seguin
2017/0239041 A1 8/2017 Quinn
2017/0266003 A1 9/2017 Hammer et al.
2018/0028779 A1* 2/2018 von Oepen ........... A61F 2/2427
2018/0168803 A1* 6/2018 Pesce ...................... A61F 2/246
2018/0228610 A1 8/2018 Lashinski et al.
2018/0235791 A1 8/2018 Kang et al.
2019/0029811 A1 1/2019 Bishop et al.
2019/0083263 A1 3/2019 Hariton et al.
2019/0209297 A1 7/2019 Metchik et al.
2020/0155332 A1* 5/2020 Longo ..................... A61F 2/958
2020/0155798 A1* 5/2020 Yang ...................... A61N 1/057
2020/0155804 A1* 5/2020 von Oepen ........... A61F 2/2439
2020/0254160 A1* 8/2020 Stack ................. A61B 17/3468
2020/0360141 A1* 11/2020 Stappenbeck ......... A61F 2/9517
2020/0367871 A1* 11/2020 Van Hoven ...... A61B 17/00234
2021/0001085 A1* 1/2021 Schmidt ............ A61B 17/3468
2021/0077257 A1* 3/2021 Vesely .................... A61F 2/243
2021/0283373 A1* 9/2021 Porter ............... A61M 25/0136
2021/0322166 A1* 10/2021 von Oepen ........... A61F 2/2433
2022/0054269 A1 2/2022 Khairkhahan
2022/0160997 A1* 5/2022 Hou ....................... A61B 90/37
2022/0192630 A1* 6/2022 Schmidt .............. A61M 25/104
2022/0280297 A1* 9/2022 Zhang .................. A61F 2/2436
2023/0001150 A1* 1/2023 Tang ...................... A61B 50/20
2023/0080273 A1* 3/2023 Winston ................ A61F 2/2427 623/2.11
2023/0330390 A1* 10/2023 Schmidt ............ A61M 25/0108
2024/0091491 A1* 3/2024 Davis ................ A61M 25/0041
2024/0350772 A1* 10/2024 Shao ................. A61B 18/1492
2025/0049424 A1* 2/2025 Willenbrink ....... A61B 17/3417
2025/0249215 A1* 8/2025 Gabay ............... A61M 25/0147
2025/0367408 A1* 12/2025 Monteon ............... A61F 2/2436
2026/0048236 A1* 2/2026 Slam ................. A61M 25/0136

FOREIGN PATENT DOCUMENTS

CA 2729027 A1 12/2009
CA 2863939 A1 8/2012
CA 2842288 A1 1/2013
CA 2871156 A1 11/2013
CA 2872611 A1 11/2013
CN 101484093 A 7/2009
CN 102781371 A 11/2012
CN 102858272 A 1/2013
CN 202821715 U 3/2013
CN 105455924 A 4/2016
CN 104768500 B 10/2017
CN 109846579 A 6/2019
DE 102013017750 A1 4/2015
DE 102013017993 A1 6/2015
EP 1796597 A2 6/2007
EP 2032078 A1 3/2009
EP 2032080 A2 3/2009
EP 2150206 A1 2/2010
EP 2465568 A1 * 6/2012 ........ A61M 25/0136
EP 2849681 A1 3/2015
EP 1871300 B1 4/2016
EP 3023117 A1 5/2016
EP 3042615 A1 7/2016
EP 3056170 A1 8/2016
EP 2023858 B1 10/2016
EP 3081195 A1 10/2016
EP 2032080 B1 5/2017
EP 3187150 A1 7/2017
EP 3241525 A1 11/2017
ES 2586111 T3 10/2016
JP 2013517830 A 5/2013
JP 2016512721 A 5/2016
JP 2016512726 A 5/2016
JP 2016521633 A 7/2016
RU 2014153781 A 7/2016
WO 9640347 A1 12/1996
WO 0060995 A2 10/2000
WO 03059209 A2 7/2003
WO 2004112658 A1 12/2004
WO 2005087140 A1 9/2005
WO 2006064490 A1 6/2006
WO 2006102329 A1 9/2006
WO 2006111391 A1 10/2006
WO 2007016097 A2 2/2007
WO 2007050256 A2 5/2007
WO 2007078772 A1 7/2007
WO 2007144865 A1 12/2007
WO 2008141322 A1 11/2008
WO 2009026563 A2 2/2009
WO 2009053952 A2 4/2009
WO 2011034973 A3 5/2011
WO 2012035279 A1 3/2012
WO 2013016618 A2 1/2013
WO 2013028387 A2 2/2013
WO 2015123597 A1 8/2015
WO 2016000274 A1 1/2016
WO 2016050751 A1 4/2016
WO 2016059533 A1 4/2016
WO 2016079734 A1 5/2016
WO 2016130706 A1 8/2016

(56) References Cited

FOREIGN PATENT DOCUMENTS

| | | | | |
|---|---|---|---|---|
| WO | 2017079234 | A1 | 5/2017 | |
| WO | 2017091605 | A1 | 6/2017 | |
| WO | 2019119674 | A1 | 6/2019 | |
| WO | 2019154927 | A1 | 8/2019 | |
| WO | 2021024183 | A1 | 2/2021 | |
| WO | WO-2022261022 | A1 * | 12/2022 | ............ A61M 29/00 |
| WO | 2023026113 | A1 | 3/2023 | |

OTHER PUBLICATIONS

Campelo-Parada, et al., First-in-Man Experience of a Novel Transcatheter Repair System for Treating Severe Tricuspid Regurgitation, J. Am. Coll. Cardiol., 66(22):2475-83 (2015).
Espiritu, et al., Transcatheter Mitral Valve Repair Therapies: Evolution, Status and Challenges, Annals of Biomedical Engineering, 45(2):332-359 (2017).
Extended EP Search Report dated Sep. 7, 2018 in EP Patent Application Serial No. 18165070.6.
International Search Report Written Opinion dated Nov. 17, 2020 in Int'l PCT Patent Appl. Serial No. PCT/IB2020/057368.
International Search Report Written Opinion dated Dec. 20, 2022 in Int'l PCT Patent Appl. Serial No. PCT/IB2022/056960.
International Search Report and Written Opinion dated Jul. 10, 2019 in Int'l PCT Patent Appl. Serial No. PCT/EP2019/053038.
International Search Report dated Dec. 1, 2015 in Intl PCT Patent Appl. No. PCT/EP2015/072388.
Peppas, et al., Preclinical in vivo long-term evaluation of the novel Mitra-Spacer technology: experimental validation in the ovine model, EuroIntervention, 13(3):272-279 (2017).

* cited by examiner

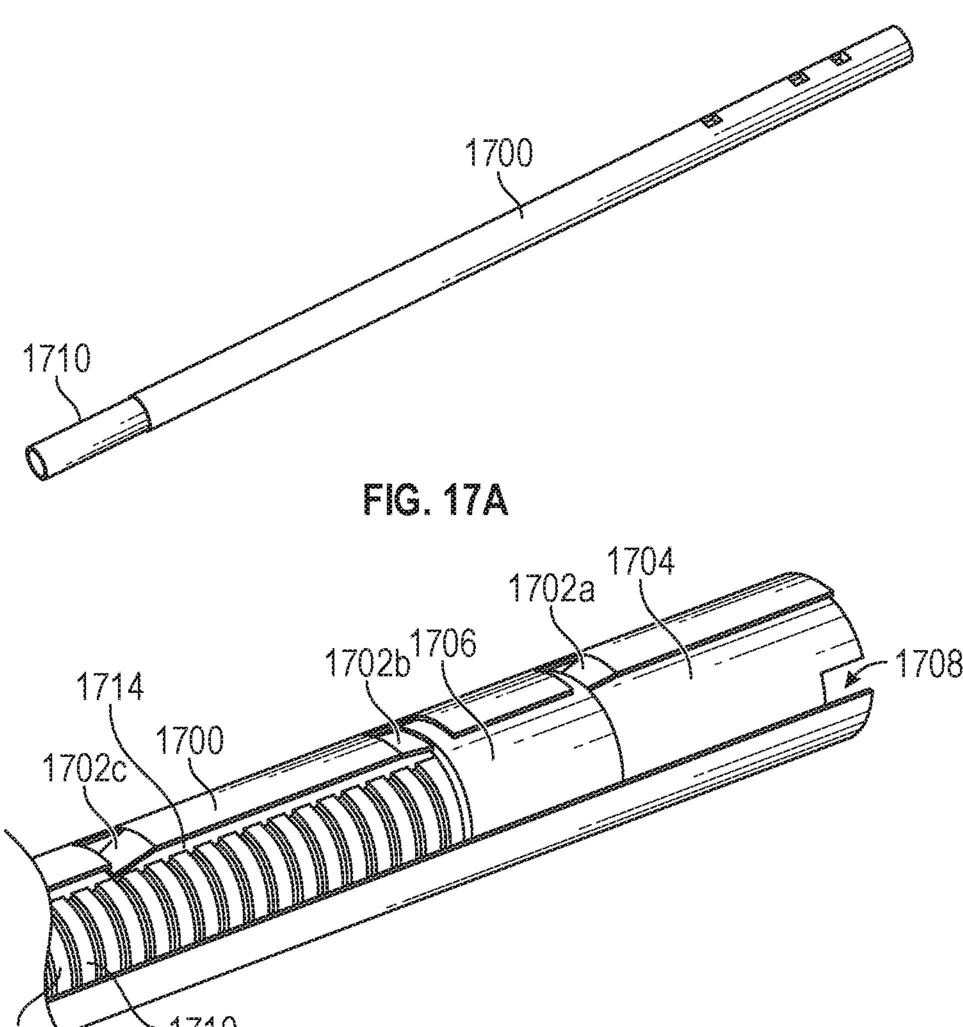
FIG. 17A
FIG. 17B
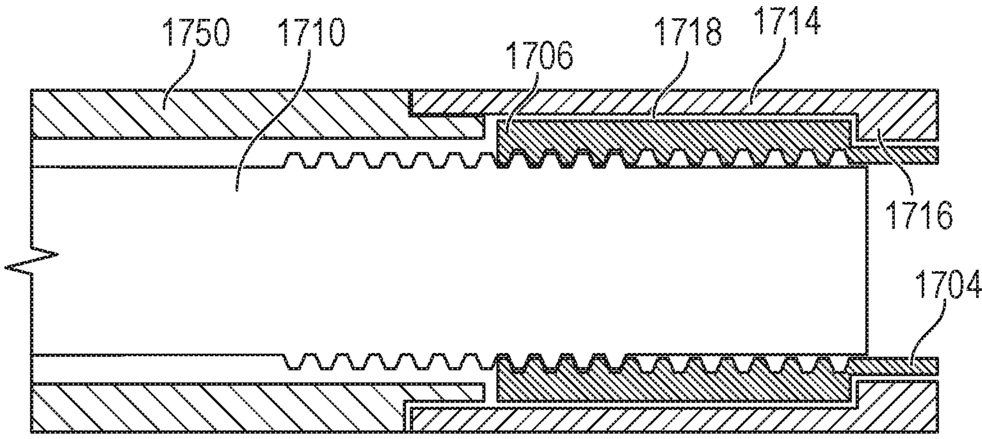
FIG. 17C

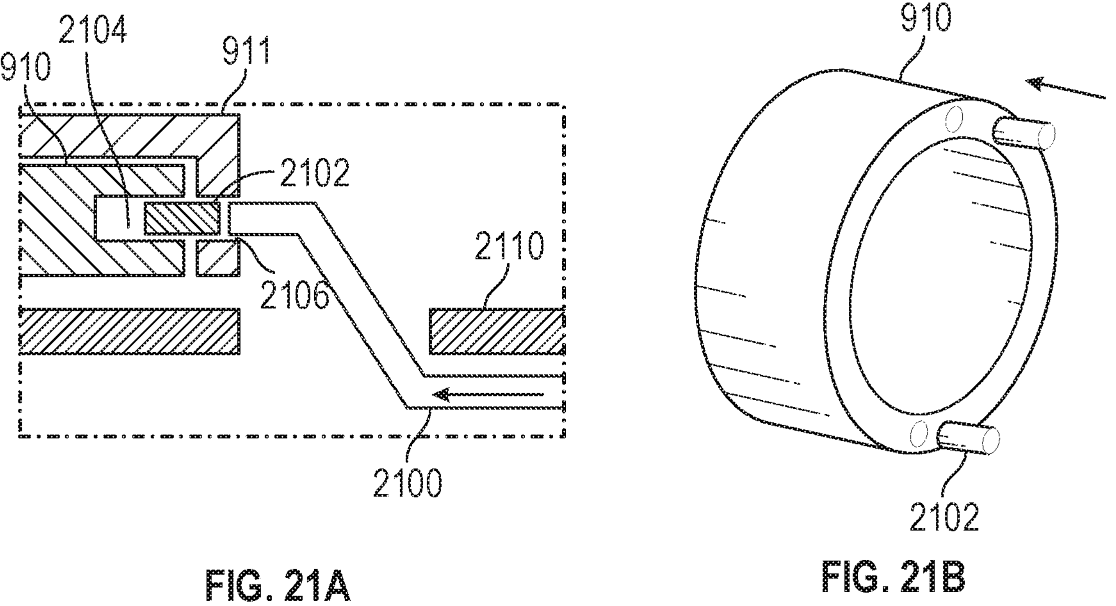
FIG. 21A
FIG. 21B
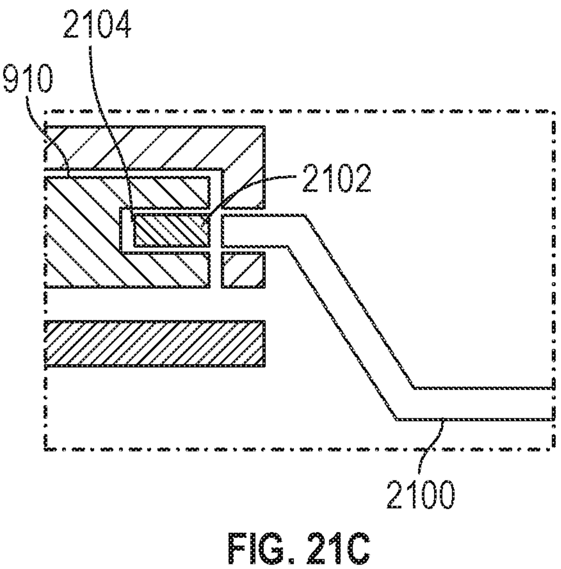
FIG. 21C

SYSTEMS AND METHODS FOR DELIVERING PROSTHETICS TO TREAT A CARDIAC VALVE

CROSS-REFERENCE TO RELATED APPLICATIONS

This application is a national phase application under 35 U.S.C. § 371 of PCT/IB2022/056960, filed Jul. 27, 2022, which claims priority to U.S. Provisional Application Ser. No. 63/226,683, filed Jul. 28, 2021, the entire contents of each of which are incorporated herein by reference.

FIELD OF USE

The present disclosure is directed to apparatus and methods for performing transcatheter or minimally invasive repair of a defective cardiac valve, such as the tricuspid, mitral, pulmonary, and aortic valves.

BACKGROUND

The human heart has four major valves which moderate and direct blood flow in the cardiovascular system. These valves serve critical functions in assuring a unidirectional flow of an adequate blood supply through the cardiovascular system. The mitral valve and aortic valve control the flow of oxygen-rich blood from the lungs to the body. The mitral valve lies between the left atrium and left ventricle, while the aortic valve is situated between the left ventricle and the aorta. Together, the mitral and aortic valves ensure that oxygen-rich blood received from the lungs is ejected into systemic circulation. The tricuspid and pulmonary valves control the flow of oxygen-depleted blood from the body to the lungs. The tricuspid valve lies between the right atrium and right ventricle, while the pulmonary valve is situated between the right ventricle and the pulmonary artery. Together the tricuspid and pulmonary valves ensure unidirectional flow of oxygen-depleted blood received from the right atrium towards the lungs.

Heart valves are passive structures composed of leaflets that open and close in response to differential pressures on either side of the valve. The aortic, pulmonary, and tricuspid valves have three leaflets, while the mitral valve has only two leaflets. Dysfunction of the cardiac valves is common and can have profound clinical consequences. Regurgitation occurs when the valve leaflets do not meet, or "coapt" correctly, thus causing blood to leak backwards through the valve each time the heart pumps. Failure of the valves to prevent regurgitation leads to an increase in the pressure of blood in the lungs or liver and reduces forward blood flow, causing the heart to pump more blood to compensate for the loss of pressure. Such degradation may result in serious cardiovascular compromise or even death. Valvular dysfunction either results from a defect in the valve leaflet or supporting structure, or dilation of the fibrous ring supporting the valve. These factors lead to poor coaptation of valve leaflets, allowing blood to travel in the wrong direction.

Previously known medical treatments to address diseased valves generally involve either repairing the diseased native valve or replacing the native valve with a mechanical or biological valve prosthesis. Previously-known valve prostheses have some disadvantages, such as the need for long-term maintenance with blood thinners, the risk of clot formation, limited durability, etc. Accordingly, valve repair, when possible, usually is preferable to valve replacement. However, most dysfunctional valves are too diseased to be repaired using previously known methods and apparatus. Accordingly, a need exists for a prosthesis capable of assisting heart valve function that enables treatment of a larger patient population, while reducing the need to fully supplant the native heart valve.

For many years, the standard treatment for such valve dysfunction called for surgical repair or replacement of the valve during open-heart surgery, a procedure conducted under general anesthesia. An incision is made through the patient's sternum (sternotomy), and the heart is accessed and stopped while blood flow is rerouted through a heart-lung bypass machine. When replacing the valve, the native valve is excised and replaced with either a mechanical or biological prosthesis. However, these surgeries are prone to many complications and long hospital stays for recuperation.

More recently, transvascular techniques have been developed for introducing and implanting a replacement valve, using a flexible catheter in a manner less invasive than open-heart surgery. In such techniques, a replacement valve is mounted in a compressed state at the end of a flexible catheter and advanced through the blood vessel of a patient until the prosthetic valve reaches the implantation site. The valve then is expanded to its functional size at the site of the defective native valve, usually by inflating a balloon within where the valve has been mounted. By expanding the prosthetic valve, the native valve leaflets are generally pushed aside and rendered ineffective. Examples of such devices and techniques, wherein the native valve is replaced in its entirety by a substitute tissue valve, are described, for example, in U.S. Pat. Nos. 6,582,462 and 6,168,614 to Andersen.

Prostheses have been produced and used for over sixty years to treat cardiac disorders. They have been made from a variety of materials, both biological and artificial. Mechanical or artificial valves generally are made from non-biological materials, such as plastics or metals. Such materials, while durable, are prone to blood clotting and thrombus formation, which in turn increases the risk of embolization and stroke or ischemia. Anticoagulants may be taken to prevent blood clotting that may result in thromboembolic complications and catastrophic heart failure, however, such anti-clotting medication may complicate a patient's health due to the increased risk of hemorrhage.

In contrast, "bio-prosthetic" valves are constructed with prosthetic leaflets made of natural tissue, such as bovine, equine or porcine pericardial tissue, which functions very similarly to the leaflets of the natural human heart valve by imitating the natural action of the heart valve leaflets, coapting between adjacent tissue junctions known as commissures. The main advantage of valves made from tissue is they are not as prone to blood clots and do not absolutely require lifelong systemic anticoagulation.

In recent years, bio-prosthetic valves have been constructed by integrating prosthetic leaflets made from natural tissue into a stent-like supporting frame, which provides a dimensionally stable support structure for the prosthetic leaflets. In more advanced prosthetic heart valve designs, besides providing dimensionally stable support structure for the prosthetic leaflets, the stent-like supporting frame also imparts a certain degree of controlled flexibility, thereby reducing stress on the prosthetic leaflet tissue during valve opening and closure and extending the lifetime of the prosthetic leaflets. In most designs, the stent-like supporting frame is covered with a biocompatible cloth (usually a polyester material such as Dacron™ or polytetrafluoroethylene (PTFE)) that provides sewing attachment points for the prosthetic leaflet commissures and prosthetic leaflets themselves. Alternatively, a cloth-covered suture ring may be attached to the stent-like supporting frame, providing a site for sewing the valve structure in position within the patient's heart during a surgical valve replacement procedure.

While iterative improvements have been made on surgical bio-prosthetic valves over the last several decades, existing bio-prosthetic valves still have drawbacks. In most designs, the bio-prosthetic valve is implanted as a replacement for the native valve, filling the entire space the native valve had occupied. One drawback to this procedure is the mismatch in size and mass between opposing surfaces of the stent-like supporting frame. The mismatch is often due to the variability in the shapes and mechanical characteristics of the stent-like supporting frame. For prosthetic valves with balloon-expandable stent-like supporting frames, the recoil of the supporting frames post-balloon-inflation may lead to perivalvular leaks around the circumference of the prosthetic valve and potential slippage and migration of the valve post-implantation. Another risk associated with prosthetic valves having balloon-expandable supporting frames is potential damage to the prosthetic leaflets of the prosthesis during implantation, when the prosthetic leaflets may be compressed between the balloon and the supporting frame. For prosthetic valves with self-expanding stent-like supporting frames, mismatch may arise due to the deformation/movement of the supporting frame, e.g., slight deformation of the frame into a less than circular shape during normal cardiac movement. Such mismatch may lead to instability among components of a prosthetic valve, resulting in perivalvular leaks and uneven stress distribution in the prosthetic leaflets, resulting in accelerated wear of the valve.

Some innovation has addressed these problems by augmenting, rather than replacing, the native valve. The simplest of these devices is a plug suspended across the center of the valve that allows the native leaflets to coapt against the plug body to block regurgitation, as described in U.S. Pat. No. 7,854,762 to Speziali. Though the plug design helps to prevent regurgitation, the major drawback is that it also blocks some of the blood flow during diastole. Improved prostheses are described in U.S. Pat. Nos. 10,383,729, 10,682,231, 10,987,220 to Quinn, U.S. Pat. No. 10,952,854 to Heneghan, and U.S. Patent Application Publication No. 2021/0077257 to Vesely, the entire contents of each of which are incorporated herein by reference.

Accessing the tricuspid valve with a replacement heart valve via a transfemoral venous access route is a desired option given the familiarity of physicians with this anatomical delivery pathway, and its conventional use in clinical practice. However, from a design and engineering perspective the transfemoral venous access route provides challenges due to some acute bends and angles the heart valve replacement device needs to traverse.

In view of the foregoing drawbacks of previously known systems and methods, there exists a need for improved systems and methods for delivering prosthetics to a defective heart valve.

SUMMARY

The present disclosure overcomes the drawbacks of previously-known systems and methods by providing systems and methods for implanting a therapeutic heart valve device at a native heart valve of a patient's heart. The system may include a prosthetic device that may be implanted at the native heart valve, and a support structured to maintain the prosthetic device at the native heart valve. In some embodiments, the support includes a first adjustable bend having a preformed bend, which may be actuated to adjust a position of the prosthetic device along a first plane, and a second adjustable bend proximal to the first adjustable bend, which may be actuated to adjust the position of the prosthetic device along a second plane. The orientation of the first plane is dependent on the position of the prosthetic device along the second plane. For example, the first and second adjustable bends may be actuated to adjust the position of the prosthetic device along the first and second planes to facilitate navigation of the prosthetic device through the patient's inferior vena cava (IVC) and right atrium to the patient's tricuspid valve.

In addition, the support further may include an elongated rail extending concentrically through, and which may be coupled to, the prosthetic device, the elongated rail having the preformed bend and a first flexibility. Moreover, the support may include a first shaping catheter slidably disposed over the elongated rail such that movement of the first shaping catheter over the preformed bend of the elongated rail adjusts an angle of the first adjustable bend. The first shaping catheter may have a second flexibility less flexible than the first flexibility. The first shaping catheter may have a distal portion having a first stiffness and a proximal portion having a second stiffness more stiff than the first stiffness, such that movement of the distal portion of the first shaping catheter over the preformed bend does not adjust the angle of the first adjustable bend, whereas movement of the proximal portion of the first shaping catheter over the preformed bend adjusts the angle of the first adjustable bend, thereby minimizing damage to the support.

Moreover, the elongated rail may have the second adjustable bend having a second preformed bend. Accordingly, the support further may include a second shaping catheter slidably disposed over the first shaping catheter such that movement of the second shaping catheter over the second preformed bend of the elongated rail adjusts an angle of the second adjustable bend. The second bend shaping catheter may have a third flexibility less flexible than the second flexibility. Additionally, the second shaping catheter may have a distal portion having a first stiffness and a proximal portion having a second stiffness more stiff than the first stiffness, such that movement of the distal portion of the second shaping catheter over the second preformed bend does not adjust the angle of the second adjustable bend, whereas movement of the proximal portion of the second shaping catheter over the second preformed bend adjusts the angle of the second adjustable bend, thereby minimizing damage to the support.

In addition, the support further may include a valve support catheter slidably disposed over the second shaping catheter and coupled to the prosthetic device. The valve support catheter may have a fourth flexibility more flexible than the first flexibility, such that movement of the valve support catheter relative to the native heart valve adjusts a depth of the prosthetic device relative to the native heart valve without adjusting, or minimally adjusting, the position of the first and second adjustable bends. Moreover, the elongated rail may include an elongated rail distal portion extending concentrically through and coupled to the prosthetic device and an elongated rail proximal portion that may be attached to the elongated rail distal portion during delivery of the prosthetic device, and detached from the elongated rail distal portion for implantation of the elongated rail distal portion and the prosthetic device.

Additionally, the first shaping catheter may include a first shaping catheter distal portion and a first shaping catheter proximal portion that may be attached to the first shaping catheter distal portion during delivery of the prosthetic device, and detached from the first shaping catheter distal portion for implantation of the first shaping catheter distal portion. The first shaping catheter distal portion may include a lock for locking the first shaping catheter distal portion to the elongated rail distal portion. Moreover, the second shaping catheter may include a second shaping catheter distal portion and a second shaping catheter proximal portion that may be attached to the second shaping catheter distal portion during delivery of the prosthetic device, and detached from the second shaping catheter distal portion for implantation of the second shaping catheter distal portion. The second shaping catheter distal portion may include a lock for locking the second shaping catheter distal portion to the first shaping catheter distal portion.

The prosthetic device may include a spine configured to be coupled to a distal region of the support via a spine connector. For example, the spine connector may include a plurality of ridges disposed at a proximal region of the spine, and the support may be configured to expand responsive to an external stimulus, such that the distal region of the support is configured to be disposed over the plurality of ridges in an expanded state and coupled to the proximal region of the spine via an interference fit between an inner surface of the distal region of the support and the plurality of ridges upon removal of the external stimulus. Alternatively, the spine connector may include an elongated rod having a proximal end coupled to the distal region of the support and a distal end having one or more collapsible prongs. The one or more collapsible prongs may have a protrusion, and a distal region of the spine may have one or more grooves sized and shaped to receive the protrusion when the one or more collapsible prongs are in an expanded state. Accordingly, the spine may be configured to be disposed over the distal end of the spine connector when the one or more collapsible prongs are in a collapsed state until a proximal end of the spine abuts an abutment disposed at the distal region of the support and the protrusion engages the one or more grooves in the expanded state, thereby prevent relative movement between the spine and the spine connector.

Alternatively, the spine connector may include an elongated rod having a proximal end coupled to the distal region of the support and a distal end configured to be coupled to a plug having a distal abutment. Accordingly, the spine may be configured to be disposed over the distal end of the spine connector until a proximal end of the spine abuts a proximal abutment disposed at the distal region of the support. The plug may then be coupled to the distal end of the elongated rod, such that the proximal and distal abutments prevent relative axial and rotational movement between the spine and the spine connector.

Moreover, the support may include a stent sized and shaped to anchor the support to a blood vessel coupled to the heart. Accordingly, the system further may include a stent tube slidably disposed over the support. A first portion of the stent tube may be pivotally coupled to a first portion of the stent, and a second portion of the stent tube may be moveably coupled to a second portion of the stent, such that movement of the second portion of the stent tube along the second portion of the stent causes the stent tube to pivot about the first portion of the stent to thereby adjust an angle of the second adjustable bend. For example, the second portion of the stent may include a rail such that the second portion of the stent tube is moveable along the rail. Alternatively, the second portion of the stent tube may freely move relative to the stent such that the stent tube pivots about the first portion of the stent responsive to movement of the prosthetic device throughout multiple cardiac cycles. Alternatively, in some embodiments, the stent tube may have a first portion rigidly coupled to a first portion of the stent and a second portion rigidly coupled to a second portion of the stent such that the stent tube does not move relative to the stent throughout multiple cardiac cycles.

In some embodiments, the stent may include a stent spine having one or more flexible guiding portions configured to transition between a radially collapsed state and a radially expanded state. Accordingly, the system further may include a stent support catheter slidably disposed over the one or more flexible guiding portions in the radially expanded state, such that the one or more flexible guiding portions may be biased toward the radially collapsed state. The one or more flexible guiding portions may be configured to receive the support therethrough in the radially expanded state within the stent support catheter, such that upon removal of the stent support catheter, the one or more flexible guiding portions are configured to clamp the support.

The stent spine may include a central guiding portion configured to be slidably disposed within the stent support catheter, and further configured to receive the support therethrough. Moreover, the one or more flexible guiding portions may include at least one of one or more proximal flexible guiding portions disposed on the stent spine proximal to the central guiding portion or one or more distal flexible guiding portions disposed on the stent spine distal to the central guiding portion.

Alternatively, the stent may include a stent spine having one or more flexible guiding portions configured to transition between a radially collapsed state and a radially expanded state, and the outer surface of the support may include one or more grooves sized and shaped to receive the one or more flexible guiding portions. Accordingly, the system further may include a stent support catheter slidably disposable between the support and the one or more flexible guiding portions in the radially expanded state. The one or more flexible guiding portions may be biased toward the radially collapsed state, such that the stent support catheter is configured to maintain the one or more flexible guiding portions in the radially expanded state as the stent support catheter receives the support therein. Upon removal of the stent support catheter, the one or more flexible guiding portions may be configured to transition to the radially collapsed state within the one or more grooves to thereby prevent axial movement between the stent spine and the support. Alternatively, the stent may include a stent spine having one or more compliant rings. Accordingly, the system further may include a stent support catheter configured to be received through and expand the one or more compliant rings to a radially expanded state, and further configured to slidably receive the support therein, such that, upon removal of the stent support catheter, the one or more compliant rings may be configured to clamp the support.

In some embodiments, the stent may include a stent tube slidably disposed over the support, and an outer surface of a proximal region of the support may include a first threaded surface. Accordingly, the system further may include a rotatable driver disposed within the stent tube. For example, the rotatable driver may have a lumen sized and shaped to receive the proximal region of the support therein, such that an inner surface of the rotatable driver includes a second threaded surface configured to rotatably engage with the first threaded surface of the proximal region of the support. The rotatable driver may be axially controlled relative to the stent tube and the support is rotationally fixed relative to the stent tube, such that rotation of the rotatable driver causes translational movement of the support relative to the stent tube via the first and second threaded surfaces. The rotatable driver may include a shoulder portion, and the outer surface of the proximal region of the support may include a rail portion. Moreover, the stent tube may include one or more pairs of inward facing flaps configured to lock the shoulder portion of the rotatable driver to axially control the rotatable driver relative to the stent tube, and one or more inward facing tabs configured to slidably engage with the rail portion to rotationally fix the support relative to the stent tube. Alternatively, the rotatable driver may include a shoulder portion, and an inner surface of the stent tube may include a groove sized and shaped to receive the shoulder portion therein to thereby axially control the rotatable driver relative to the stent tube.

Moreover, the stent may include an expandable wire frame having a proximal draping portion and distal draping portion. The distal draping portion may have more flexibility than the proximal draping portion of the expandable wire frame. For example, the expandable wire frame may include strut rings each extending around a circumference of the stent, such that the strut rings in the distal draping portion are thinner than the strut rings in the proximal draping portion.

In accordance with another aspect of the present disclosure, a delivery catheter handle for implanting the prosthetic device at the native heart valve of the patient's heart via the support operatively coupled to the delivery catheter handle is provided. As described above, the support includes a distal, implantable portion coupled to the prosthetic device and a proximal, delivery portion that may be releasably attached to the distal, implantable portion during delivery of the prosthetic device. The delivery catheter handle includes a first portion operatively coupled to the prosthetic device via the support, and a second portion. The handle further includes a first set of actuators disposed on at least one of the first or second portions, which may be actuated to adjust a directional position of the prosthetic device relative to the native heart valve. In addition, the handle may include a second set of actuators disposed on at least one of the first or second portions, which may be actuated to lock the distal, implantable portion of the support and to detach the distal, implantable portion from the proximal, delivery portion for implantation of the distal, implantable portion and the prosthetic device. Moreover, the handle may include a locking mechanism that may be unlocked such that the first portion is rotatable relative to the second portion, wherein rotation of the first portion causes rotation of the prosthetic device relative to the second portion of the handle.

The first portion may be rotatably coupled to the second portion via a rod. The rod may be fixed axially relative to the first portion. Moreover, an actuator of the first set of actuators may be configured to be actuated to axially move the first portion relative to the second portion along the rod to adjust an axial distance of the prosthetic device relative to the second portion. In addition, an actuator of the second set of actuators may be configured to be actuated to lock the distal, implantable portion of the support. The delivery catheter further may include an axial control mechanism disposed within the rod and configured to prevent a predefined additional amount of axial movement of the first portion relative to the second portion until the actuator of the second set of actuators has been fully actuated to lock the distal, implantable portion of the support.

For example, the axial control mechanism may include a retention clip configured to be collapsed radially inward responsive to an axial force by the rod upon actuation of the actuator of the second set of actuators. Accordingly, the axial control mechanism may be slidably disposed within the rod between a first position where the retention clip prevents distal movement of the axial control mechanism relative to the rod, and a second position where the axial force applied to the retention clip by the rod upon actuation of the actuator of the second set of actuators causes the retention clip to collapse radially inward to permit distal movement of the axial control mechanism relative to the rod. Additionally, the rod may include a safety clip configured to be collapsed radially inward responsive to a first axial force by the second portion upon actuation of the actuator of the first set of actuators, and the axial control mechanism may include an opening sized and shaped to receive the safety clip. Accordingly, the axial control mechanism may be slidably disposed within the rod between a first position where the opening is not aligned with the safety clip such that the axial control mechanism prevents the clip from collapsing radially inward, and a second position where a second axial force applied to the axial control mechanism upon actuation of the actuator of the second set of actuators causes the opening to align with the safety clip to permit the safety clip to collapse radially inward through the opening responsive to the first axial force applied to the safety clip by the second portion upon actuation of the actuator of the first set of actuators.

In some embodiments, the axial control mechanism may include a slider component, and an interlock component axially fixed relative to the rod and configured to be collapsed radially inward responsive to an axial force by the slider component upon actuation of the actuator of the second set of actuators. The interlock component may include an upper portion, a hinge portion, and a spring portion. Accordingly, the slider component may be slidably disposed between the rod and the interlock component between a first position where the upper portion of the interlock component prevents the predefined additional amount of axial movement of the first portion relative to the second portion, and a second position where the axial force applied to the hinge portion of the interlock component by the slider component upon actuation of the actuator of the second set of actuators causes the interlock component to collapse radially inward via contact of the spring portion with a guide rail of the rod, thereby disengaging the upper portion of the interlock component from the first portion to permit the predefined additional amount of axial movement of the first portion relative to the second portion upon actuation of the actuator of the first set of actuators.

Alternatively, the rod may include a safety clip configured to be collapsed sideways responsive to an axial force by the axial control mechanism upon actuation of the actuator of the second set of actuators. In addition, the safety clip may have a protrusion disposed thereon, and the first portion may include an opening sized and shaped to receive the protrusion therein. Accordingly, the axial control mechanism may be slidably disposed within the rod between a first position where the protrusion is not aligned with the opening such that the first portion prevents the predefined additional amount of axial movement of the first portion relative to the second portion, and a second position where the axial force applied to the axial control mechanism upon actuation of the actuator of the second set of actuators causes the safety clip to collapse sideways to align the protrusion with the opening to permit the predefined additional amount of axial movement of the first portion relative to the second portion upon actuation of the actuator of the first set of actuators.

The delivery catheter handle may include one or more pins slidably disposed within at least a portion of the first portion and the actuator of the first set of actuators. Accordingly, the axial control mechanism may be slidably disposed within the rod between a first position where the one or more pins disposed within both the first portion and the actuator of the first set of actuators, thereby preventing actuation of the actuator of the first set of actuators relative to the first portion, and a second position where an axial force applied to the one or more pins by the axial control mechanism upon actuation of the actuator of the second set of actuators causes the one or more pins to slide further into the actuator of the first set of actuators and disengage with the first portion to permit actuation of the actuator of the first set of actuators.

An actuator of the second set of actuators may be actuated to rotate and pull the proximal, delivery portion of the support relative to the distal, implantable portion to automatically detach the distal, implantable portion from the proximal, delivery portion for implantation of the distal, implantable portion and the prosthetic device. As described above, the support further may include a first adjustable bend having a preformed bend and a second adjustable bend proximal to the first adjustable bend. Accordingly, the first set of actuators may be actuated to adjust an angle of the first adjustable bend to adjust the directional position of the prosthetic device along a first plane, and to adjust an angle of the second adjustable bend to adjust the directional position of the prosthetic device along a second plane.

As described above, in some embodiments, the support further may include a stent that anchors the support to the blood vessel coupled to the heart, and a stent tube having a first portion pivotally coupled to the first portion of the stent and a second portion moveably coupled to the second portion of the stent. Accordingly, the delivery catheter handle may be actuated to move the second portion of the stent tube along the second portion of the stent to cause the stent tube to pivot about the first portion of the stent to thereby adjust the directional position of the prosthetic device along the second plane. Alternatively, the support further may include a stent that anchors the support to the blood vessel coupled to the heart, and a stent tube having a first portion pivotally coupled to the first portion of the stent and a second portion that may move freely relative to the stent. Accordingly, the stent tube may pivot about the first portion of the stent responsive to movement of the prosthetic device throughout multiple cardiac cycles.

In accordance with another aspect of the present disclosure, a device for maintaining a therapeutic heart valve device having a support at a native heart valve of a patient's heart is provided. The device may include a stent configured to anchor the support to a blood vessel coupled to the heart such that a prosthetic device coupled to the support is positioned at the native heart valve of the patient's heart. The stent may include an expandable wire frame having variable stiffness along at least one of a circumference or a length of the stent. For example, the expandable wire frame may include a first draping portion and second draping portion, wherein the first draping portion may have more flexibility than the second draping portion of the expandable wire frame to provide variable stiffness along a length of the stent. For example, the expandable wire frame may include strut rings each extending around a circumference of the stent, such that the strut rings in the first draping portion are thinner than the strut rings in the second draping portion. The device further may include the prosthetic device and the support.

Additionally or alternatively, the expandable wire frame may include a plurality of strut rings each extending around a circumference of the stent, and a plurality of longitudinally extending struts interconnecting at least some of the plurality of strut rings. The plurality of longitudinally extending struts may interconnect the plurality of strut rings in the second draping portion, but not the first draping portion to provide variable stiffness along a length of the stent. Moreover, the stent may include a stent spine configured to couple the stent to the support, and the expandable wire frame may include strut rings each extending from the stent spine around a circumference of the stent. The length of the stent struts may increase in a direction away from the stent spine to provide variable stiffness along a circumference of the stent. The device further may include the prosthetic device and the support.

BRIEF DESCRIPTION OF THE DRAWINGS

FIGS. 17A and 17B illustrate an exemplary mechanism for adjusting the position of the one or more adjustable bends of the heart valve therapeutic device constructed in accordance with the principles of the present disclosure.

FIG. 17C illustrates an alternative exemplary for adjusting the position of the one or more adjustable bends of the heart valve therapeutic device constructed in accordance with the principles of the present disclosure.

FIGS. 21A to 21C illustrate an exemplary actuator interlocking mechanism constructed in accordance with the principles of the present disclosure.

DETAILED DESCRIPTION

Figure 1:
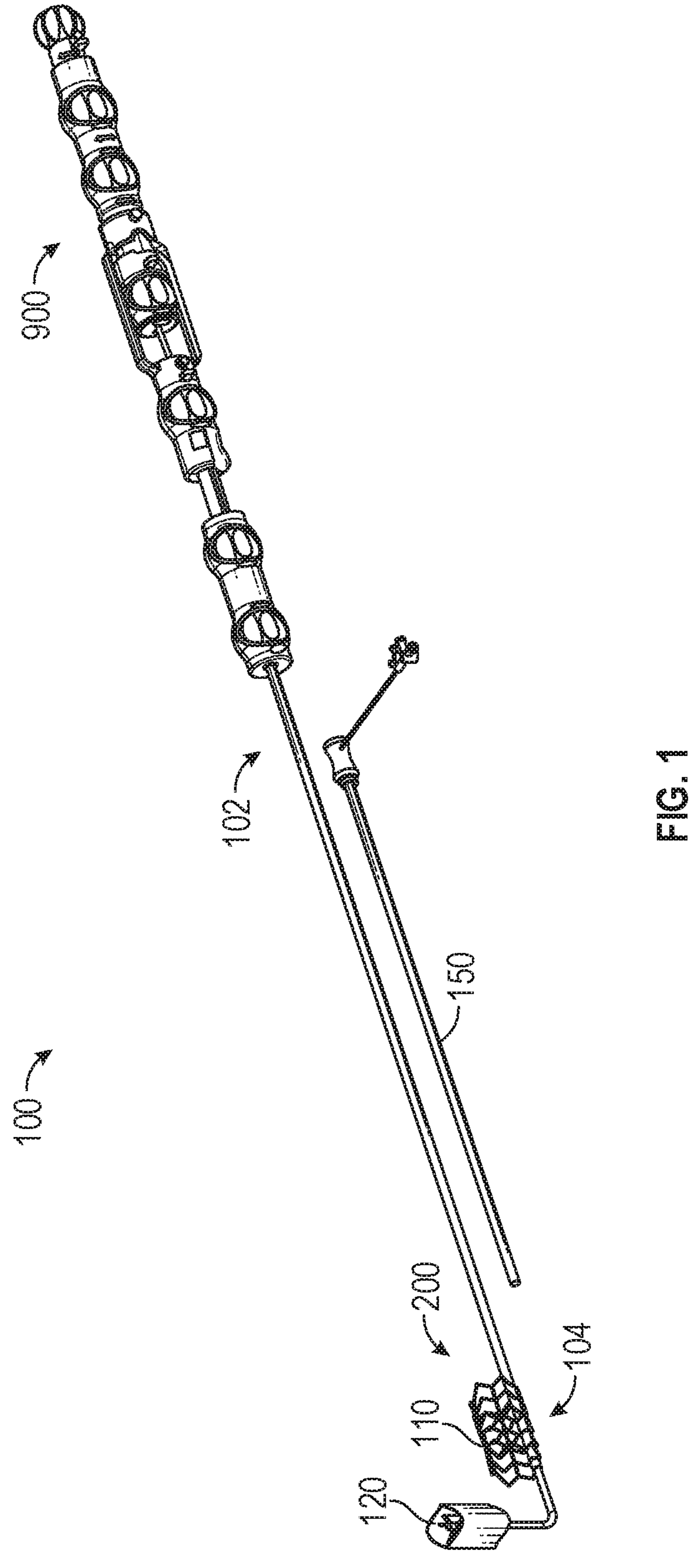
FIG. 1 is a perspective view of an exemplary heart valve therapeutic device having a double bend for repairing a defective heart valve constructed in accordance with the principles of the present disclosure.

Embodiments of the present invention are directed to exemplary systems and methods for reducing cardiac valve regurgitation. Provided herein is a prosthetic device that may contain a prosthetic coaptation body to be positioned at a native cardiac valve. The prosthetic device may be suspended across the native heart valve by a support. For example, the support may be coupled to the prosthetic coaptation body and extend out of the heart into an adjacent blood vessel coupled to the heart (e.g., superior vena cava, inferior vena cava). The support may be coupled to the blood vessel with an anchor that preferably is expandable and has a stent structure. In some examples, the support is structured to suspend the prosthetic coaptation body in the native valve in a free-standing manner without anchoring to cardiac tissue, thereby minimizing damage to the heart. The prosthetic coaptation body may be formed from a frame (e.g., metal frame such as Nitinol) that is at least partially covered by a skirt made from biocompatible material, and also includes prosthetic leaflets. The frame, biocompatible material, and prosthetic leaflets may together form a conduit through which blood flows when the prosthetic leaflets open during the cardiac cycle.

The design of the prosthetic device improves coaptation with the native heart valve leaflets and allows for a more reliable delivery. The prosthetic device may be implanted percutaneously via a blood vessel, e.g., the jugular vein, femoral vein, femoral artery, for the treatment of a defective cardiac valve, e.g., tricuspid, mitral, pulmonary, or aortic valve. In one example, the prosthetic device may be used to treat symptomatic primary or functional (secondary) tricuspid regurgitation. For example, the prosthetic device may be positioned between the native tricuspid valve leaflets to restore the valve function without altering the native anatomy or obstructing flow during diastole and held in place by an anchor system deployed in an anchor site, e.g., within the heart and/or within a blood vessel coupled to the heart such as the superior vena cava (SVC) or the inferior vena cava (IVC). Accordingly, the support may include one or more adjustable bends that may be actuated, e.g., via a handle operatively coupled to the proximal end of the support, to facilitate navigation through the patient's anatomical structures to reach the target implantation site.

The frame may be designed with predefined kink points or collapsible/expandable features to allow the conduit to be compressed into a delivery sheath without being damaged, and to more reliably expand upon delivery. The frame may have a proximal ring and a distal ring, as well as an inner ring coupled to the proximal ring via a plurality of skirt anchors to which the prosthetic valve leaflets may be attached. One or more of the rings may exhibit a scallop, sinusoidal, zig-zag shape or otherwise oscillating pattern in the expanded state to further improve the compression and expansion of the frame. The skirt of the prosthetic coaptation body may join the proximal ring to the distal ring to improve coaptation of the native valve against the skirt. The prosthetic coaptation body may be coupled to the support by a plurality of tethers that may be formed of shape-memory material such as Nitinol. The tethers may be rigid or stiff and hold the prosthetic coaptation body in position more accurately than tensile wires.

Referring to FIG. 1, an illustrative embodiment of exemplary heart valve therapeutic device 100 in accordance with the principles of the present disclosure is described. Illustratively, heart valve therapeutic device 100 is designed for repairing a defective tricuspid valve. As will be understood by a person having ordinary skill in the art, heart valve therapeutic device 100 may be readily adapted for other cardiac valves such as the mitral valve, aortic valve, or pulmonary valve.

As shown in FIG. 1, heart valve therapeutic device 100 may include prosthetic device 120 coupled to support 200 at distal region 104 of heart valve therapeutic device 100, as well as actuator 900 at proximal region 102 of heart valve therapeutic device 100. Preferably, prosthetic device 120, e.g., a prosthetic coaptation body, works together with the native leaflets to both provide a surface for the native leaflets to coapt and to provide a prosthetic valve in a conduit formed by prosthetic device 120. Unlike prior prosthetic valves that do not use the native leaflets (e.g., because they are cut away or pushed aside by the implant), prosthetic device 120 may use both the native leaflets and the prosthetic leaflets in the same native heart valve, thereby creating a "double-valve" configuration in the single heart valve. Actuator 900 may be a handle having a plurality of interfaces, e.g., knobs and switches, configured to be manipulated by a clinician to deliver the system for implantation.

Support 200 further may include anchor 110, e.g., a stent. Anchor 110 may be formed of a stent structure and is preferably collapsible in a contracted, delivery state and expandable to an expanded, deployed state to anchor prosthetic device 120 at the native cardiac valve. For example, anchor 110 may contact the inner wall of a blood vessel (e.g., the SVC or IVC) to anchor support 200 intraluminally, thereby anchoring prosthetic device 120 in a free-standing, suspended manner in the native heart valve. In addition, heart valve therapeutic device 100 may include introduction sheath 150 for facilitating delivery of prosthetic device 120, support 200, and anchor 110.

Anchor 110, prosthetic device 120, and support 200 may be constructed as described in U.S. Pat. No. 11,219,525 to Vesely, the entire contents of which are incorporated herein by reference. For example, support 200 may include a proximal, delivery portion detachably coupled to a distal, implantable portion, such that anchor 110 and prosthetic device 120 are disposed on the distal, implantable portion of support 200. During delivery, the distal, implantable portion of support 200 is coupled to the proximal, delivery portion of support 200, which is operatively coupled to actuator 900. Actuator 900 may be held and manipulated by a clinician to deliver anchor 110 and prosthetic device 120 to the target implantation site across the native valve, and to detach the distal, implantable portion of support 200 from the proximal, delivery portion of support 200, such that the distal, implantable portion of support 200 including anchor 110 and prosthetic device 120 remains implanted within the patient.

Figure 2A:
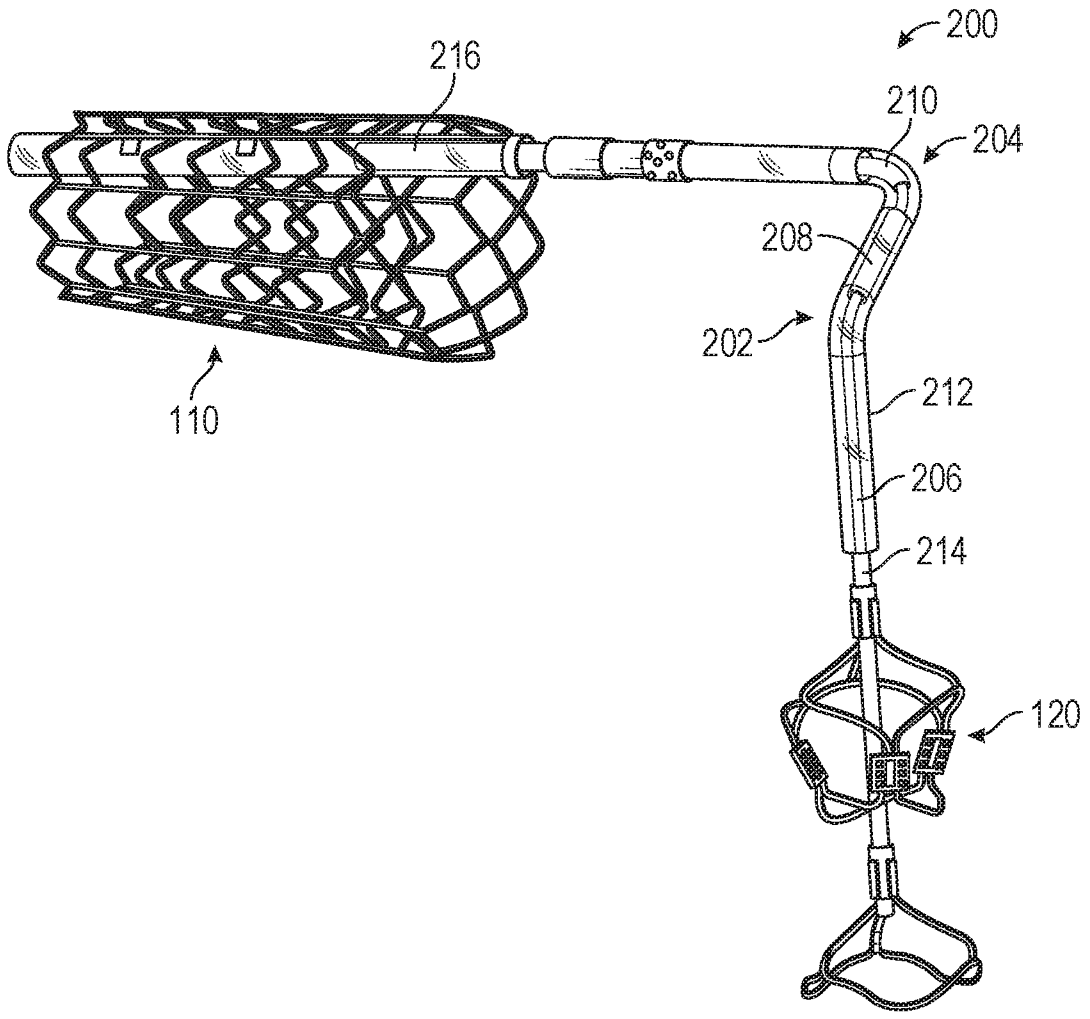
FIGS. 2A to 2C illustrate the implantable distal end of the heart valve therapeutic device of FIG. 1.
Figure 2B:
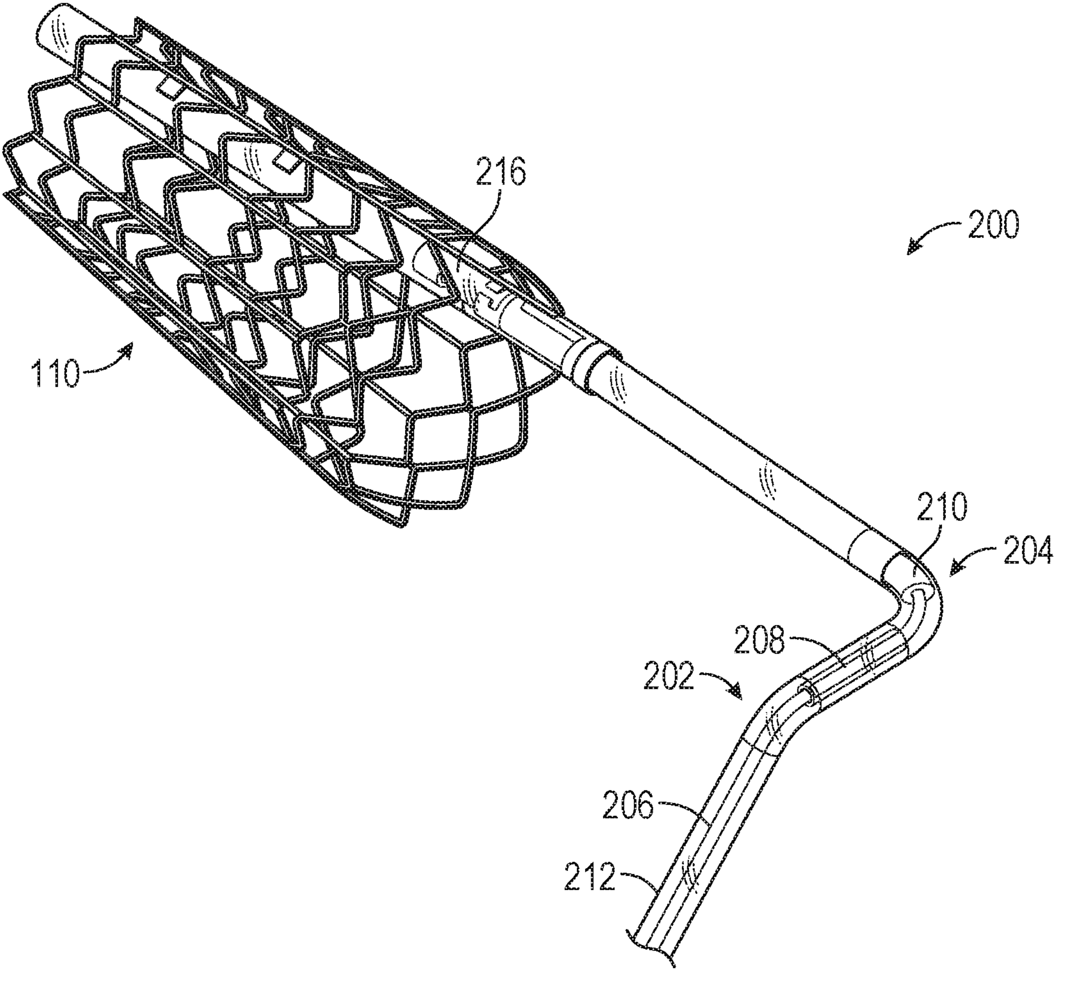
Figure 2C:
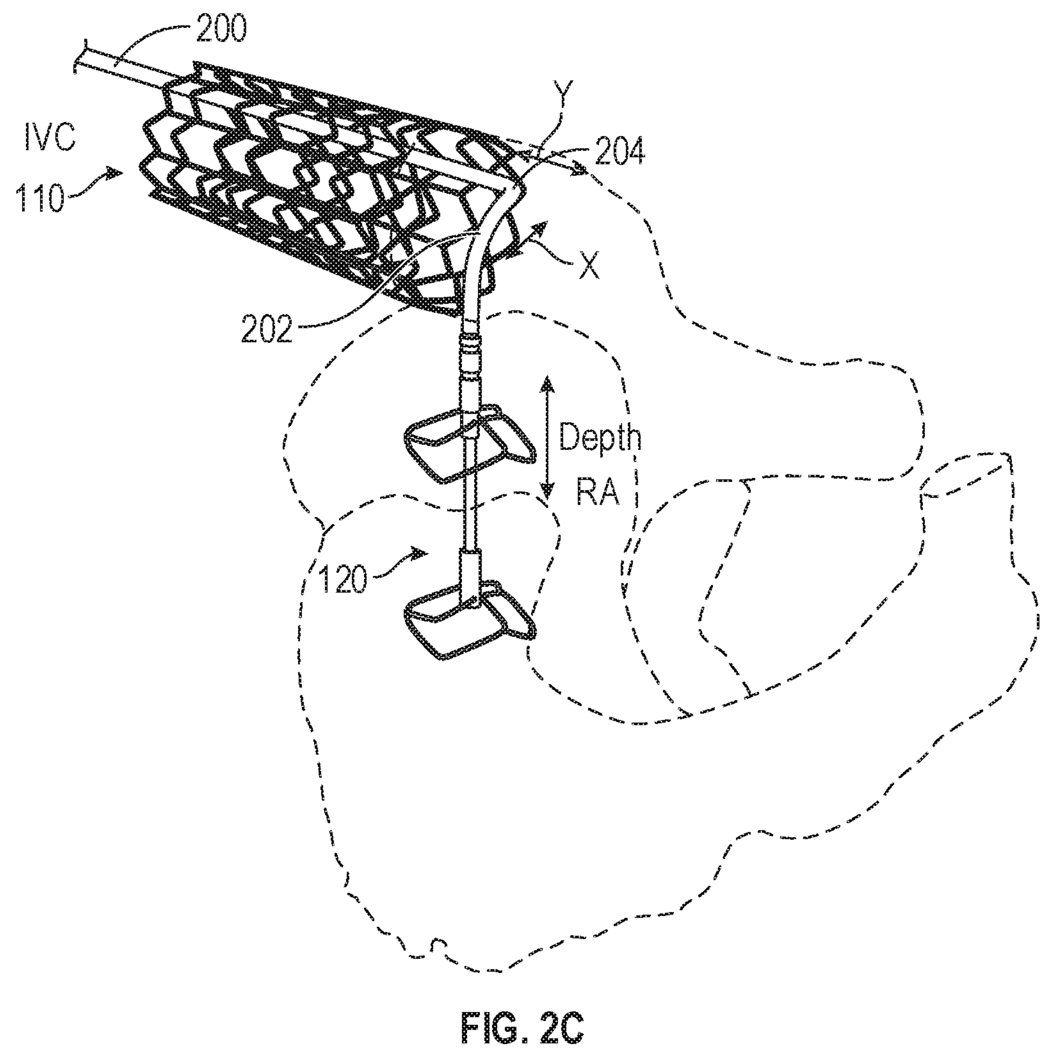

Referring now to FIGS. 2A to 2C, the distal, implantable portion of support 200 is described in further detail. As shown in FIGS. 2A and 2B, support 200 may include elongated rail 206 extending from actuator 900 to prosthetic device 120. For example, the distal end of elongated rail 206 may extend concentrically through prosthetic device 120, such that prosthetic device 120 may be slidably movable along elongated rail 206 until prosthetic device 120 is positioned at a desired location along elongated rail 206. Further, prosthetic device 120 may be locked relative to elongated railed 206 at the desired position such that prosthetic device 120 is coupled to elongated rail 206.

As shown in FIGS. 2A and 2B, elongated rail 206 may have one or more preformed bends, e.g., first preformed bend 202 and second preformed bend 204, to improve positioning of prosthetic device 120 across the native valve, as described in further detail below. For example, the bends may be predefined for a specific patient anatomy. Moreover, the preformed bends permits steering of support 200 from the predefined shape; this may have the effect of reducing stresses and strain on elongated rail 206 for long-term implant. In addition, the preformed bends may reduce the stress required to position prosthetic device 120 during delivery. For example, elongated rail 206 may be an elongated shaft made of metal (e.g., Nitinol) that is preformed in one or more areas along the length of elongated rail 206 to a predetermined angle (e.g., 50-150 degree bend, 100 degree bend). Moreover, heart valve therapeutic device 100 may include one or more radiopaque markers for in-vivo visualization during delivery of prosthetic device 120.

In addition, support 200 may include first shaping catheter 208 slidably disposed over and coaxial to elongated rail 206. The angle of first preformed bend 202 of elongated rail 206 may be based on the relative axial position between first shaping catheter 208 and elongated rail 206 responsive to actuation at handle 900. For example, as first shaping catheter 208 is advanced distally over first preformed bend 202 of elongated rail 206, the first preformed bend 202 of elongated rail 206 straightens, and as first shaping catheter 208 is retracted proximally relative to first preformed bend 202 of elongated rail 206, the elongated rail returns to its natural state with first preformed bend 202. Thus, first shaping catheter 208 may have a stiffness greater than first preformed bend 202, and accordingly, first preformed bend 202 has a flexibility that is more flexible than the flexibility of first shaping catheter 208, such that advancement of first shaping catheter 208 over first preformed bend 202 causes first preformed bend 202 of elongated rail 206 to straighten. As will be understood by a person having ordinary skill in the art, elongated rail 206 may be moved while first shaping catheter 208 remains stationary within the patient to bend and straighten elongated rail 206.

As second preformed bend 204 is proximal to first preformed bend 202, the section of first shaping catheter 208 that slides over second preformed bend 204 may have a stiffness less than second preformed bend 204, such that first shaping catheter 208 may slide over second preformed bend 204 without changing the position and angle of second preformed bend 204, whereas movement of first shaping catheter 208 over first preformed bend 202 adjusts the position and angle of first preformed bend 202 as described above.

First shaping catheter 208 may be formed of a braided, coiled, multi-durometer polymer. Alternatively, first shaping catheter 208 may be 3D printed or include a laser cut shaft. Preferably, the distal portion of first shaping catheter 208, e.g., adjacent to prosthetic device 120, may have greater flexibility along its length than the proximal portion of first shaping catheter 208, e.g., adjacent to anchor 110. Accordingly, movement of the distal portion of first shaping catheter 208 over first preformed bend 202 of elongated rail 206 may not adjust the angle of the preformed bend, whereas movement of the proximal portion of first shaping catheter 208 over first preformed bend 202 adjusts the angle of the preformed bend, thereby minimizing damage to support 200.

In addition, support 200 may include second shaping catheter 210 slidably disposed over and coaxial to first shaping catheter 208, and accordingly, to elongated rail 206. The angle of second preformed bend 204 of elongated rail 206 may be based on the relative axial position between second shaping catheter 210 and elongated rail 206 responsive to actuation at handle 900. For example, as second shaping catheter 210 is advanced distally over second preformed bend 204 of elongated rail 206, the elongated rail straightens, and as second shaping catheter 210 is retracted proximally relative to second preformed bend 204 of elongated rail 206, the elongated rail returns to its natural state with second preformed bend 204. Thus, second shaping catheter 210 may have a stiffness greater than second preformed bend 204, and accordingly, second preformed bend 204 has a flexibility that is more flexible than the flexibility of second shaping catheter 210, such that advancement of second shaping catheter 210 over second preformed bend 204 causes elongated rail 206 to straighten. As will be understood by a person having ordinary skill in the art, elongated rail 206 may be moved while second shaping catheter 210 remains stationary within the patient to bend and straighten elongated rail 206.

Like first shaping catheter 208, second shaping catheter 210 may be formed of a braided, coiled, multi-durometer polymer. Alternatively, second shaping catheter 210 may be 3D printed or include a laser cut shaft. Preferably, the distal portion of second shaping catheter 210 may have greater flexibility along its length than the proximal portion of second shaping catheter 210, e.g., adjacent to anchor 110. Accordingly, movement of the distal portion of second shaping catheter 210 over second preformed bend 204 of elongated rail 206 may not adjust the angle of the preformed bend, whereas movement of the proximal portion of second shaping catheter 210 over second preformed bend 204 adjusts the angle of the preformed bend, thereby minimizing damage to support 200. As will be understood by a person having ordinary skill in the art, elongated rail 206 may have more than two preformed bends along its length, and accordingly, support 200 may include additional shaping catheters slidably disposed over and coaxial to elongated rail 206 to adjust the position and angle of the respective preformed bends.

In addition, support 200 may include body support catheter 212 slidably disposed over and coaxial to second shaping catheter 210, and accordingly to first shaping catheter 208 and elongated rail 206. Body support catheter 212 may be formed of a braided, coiled, multi-durometer polymer. Alternatively, body support catheter 212 may be 3D printed or include a laser cut shaft. Body support catheter 212 may have high flexibility in at least the regions of first preformed bend 202 and second preformed bend 204 so as to not adjust, or only minimally adjust, the position and/or angle of first preformed bend 202 and second preformed bend 204. Preferably, body support catheter 212 does not adjust the position and/or angle of first preformed bend 202 and second preformed bend 204 as body support catheter 212 moves over first preformed bend 202 and second preformed bend 204; however, minimal adjustment thereof may occur and is acceptable. The distal end of body support catheter 212 may be coupled to prosthetic device 120, e.g., at connector 214, such that elongated rail 206 may extend concentrically through connector 214. Accordingly, body support catheter 212 may be used to deliver and adjust and finally stabilize the position of prosthetic device 120 across the native cardiac valve.

Moreover, support 200 may include anchor tube 216 coupled to anchor 110. For example, anchor tube 216 may include a first distal portion rigidly coupled to a first distal portion of anchor 110, and a second proximal portion rigidly coupled to anchor 110, such that anchor tube 216 does not move relative to anchor 110, e.g., through multiple cardiac cycles. In some embodiments, only one portion of anchor tube 216 is rigidly coupled to anchor 110 to thereby prevent relative movement between anchor tube 216 and anchor 110 through multiple cardiac cycles. Anchor tube 216 may be slidably disposed over and coaxial to body support catheter 212, and accordingly to second shaping catheter 210, first shaping catheter 208, and elongated rail 206. Anchor tube 216 permits telescoping of and anchoring of the catheter components of support 200, e.g., body support catheter 212, second shaping catheter 210, first shaping catheter 208, and elongated rail 206. Alternatively, in some embodiments, the anchor may be directly coupled to the body support catheter without the need for an anchor tube, as described in further detail below with regard to FIGS. 16A and 16B.

As shown in FIG. 2C, when anchor 110 is positioned within the IVC, support 200 may suspend prosthetic device 120 through the right atrium RA and across the native cardiac valve. Body support catheter 212 may be actuated via handle 900 to adjust the "depth" of prosthetic device 120 relative to the native cardiac valve. As described above, first shaping catheter 208 may be actuated via handle 900 to adjust the position of prosthetic device 120 by adjusting the angle of first preformed bend 202, such that the position of prosthetic device 120 is adjustable within a first plane along the "X" direction. Second shaping catheter 210 may be actuated via handle 900 to adjust the position of prosthetic device 120 by adjusting the angle of second preformed bend 204, such that the position of prosthetic device 120 is adjustable within a second plane along the "Y" direction. Accordingly, the orientation of the first plane formed along the "X" direction will be dependent on the angle of second preformed bend 204 within the second plane formed along the "Y" axis.

Figure 2D:
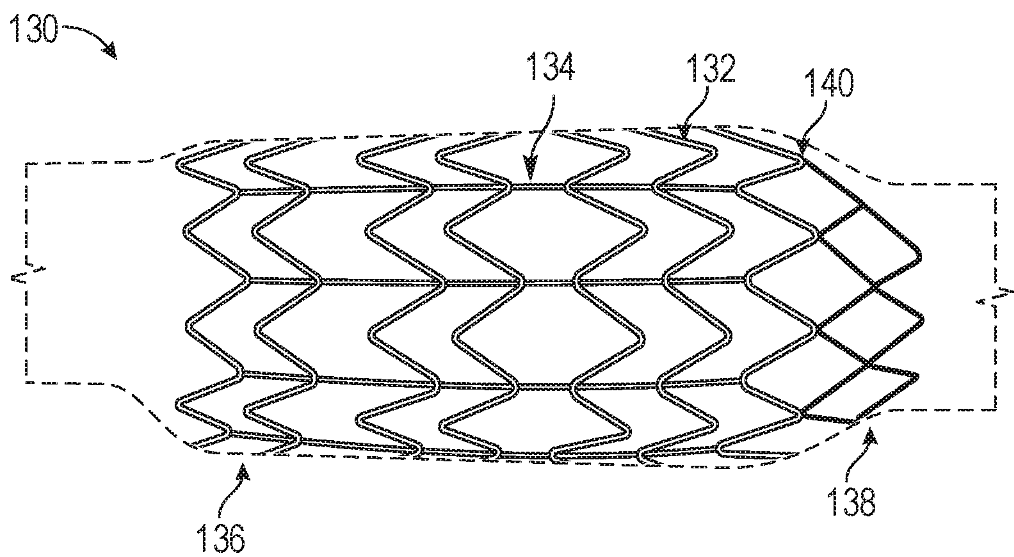
FIG. 2D illustrates an exemplary alternative anchor constructed in accordance with the principles of the present disclosure.

Referring now to FIG. 2D, an alternative exemplary anchor is provided. Like anchor 110, anchor 130 may be a stent formed of a stent structure, e.g., an expandable wire frame, and is preferably collapsible in a contracted, delivery state and expandable to an expanded, deployed state to anchor support 200 to a blood vessel coupled to the heart to thereby maintain prosthetic device 120 at the native cardiac valve. For example, anchor 130 may contact the inner wall of a blood vessel (e.g., the SVC or IVC) to anchor support 200 intraluminally, thereby maintaining prosthetic device 120 in a free-standing, suspended manner in the native heart valve.

As shown in FIG. 2D, the expandable wire frame of anchor 130 may include a plurality of strut rings 132, each extending around a circumference of anchor 130. For example, at least some of strut rings 132 may be coupled together via a plurality of longitudinal extending struts 134 to thereby define the stent structure of anchor 130. Anchor 130 may be configured to provide variability in radial stiffness along its length. For example, anchor 130 may include a first draping portion, e.g., distal draping portion 138, and a second draping portion, e.g., proximal draping portion 136, extending from apex 140, such that distal draping portion 138 has more flexibility that proximal draping portion 136. For example, as shown in FIG. 2D, the strut rings forming distal draping portion 138 may be formed of a thinner wire than the wire forming the strut rings forming at least proximal draping portion 136.

Moreover, as shown in FIG. 2D, distal draping portion 138 may be more flexible than proximal draping portion 136 as the strut rings forming distal draping portion 138 distal to apex 140 are directly coupled to each other without a plurality of longitudinal extending struts. Additionally or alternatively, anchor 130 may have radial stiffness variation with variations in diameter, strut length, and pitch. As will be understood by a person having ordinary skill in the art, in some embodiments, proximal draping portion 136 may have more flexibility than distal draping portion 138, such that the strut rings forming proximal draping portion 136 may be formed of a thinner wire than the wire forming the strut rings forming at least distal draping portion 138. Additionally or alternatively, both end regions of anchor 130 may include draping portions that have more flexibility than a middle portion of anchor 130, and/or anchor 130 may have any combination of the draping portion embodiments described herein.

Additionally or alternatively, anchor 130 may be configured to provide variability in stiffness along its circumference. For example, the wire frame forming anchor 130 may be stiffer closer to the anchor spine, e.g., where anchor 130 is coupled to support 200. For example, the length of the strut rings may vary along the circumference of anchor 130, e.g., the length may increase in a direction away from the anchor spine of anchor 130. Accordingly, anchor 130 may have variation in pitch and diameter axially, and strut length radially.

Figure 3A:
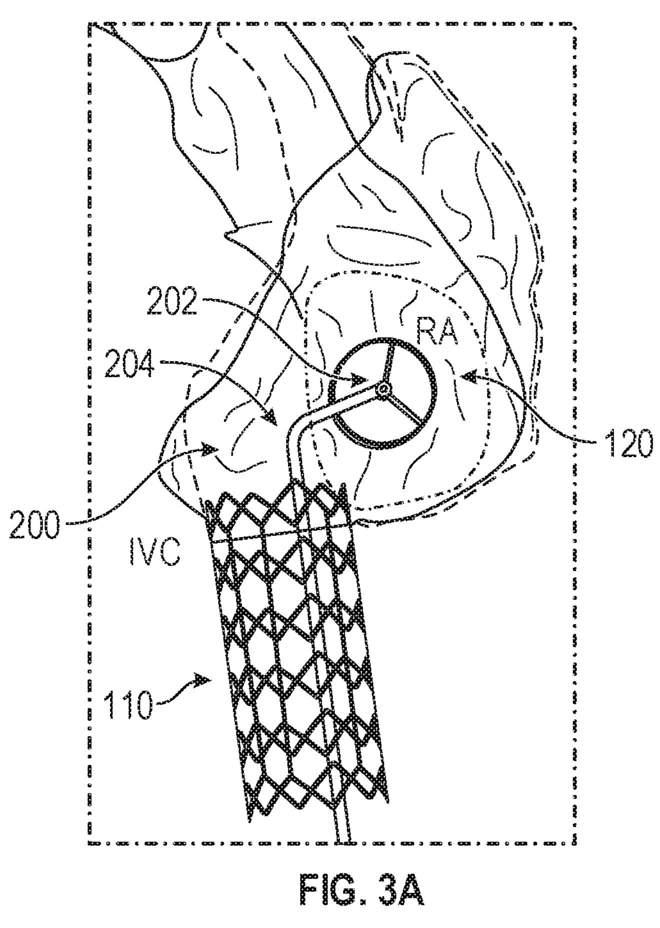
FIGS. 3A and 3B illustrate the distal end of the heart valve therapeutic device of FIG. 1 implanted within the patient in accordance with the principles of the present disclosure.
Figure 3B:
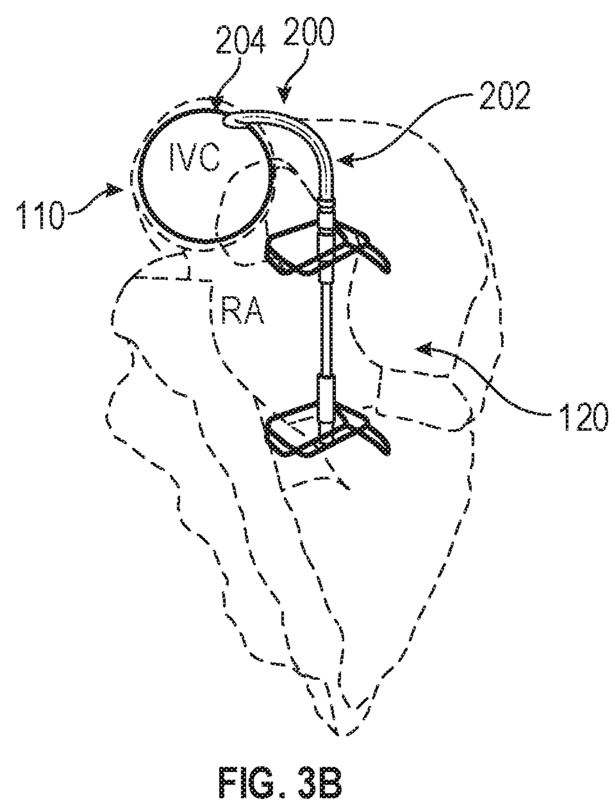

FIGS. 3A and 3B illustrate anchor 110 implanted within the patient's IVC such that support 200 suspends and maintains prosthetic device 120 across the patient's native cardiac valve. As shown in FIGS. 3A and 3B, second preformed bend 204 permits support 200 to navigate from the IVC into the RA, and first preformed bend 202 permits support 200 to navigate from the RA to be across and co-axial with the native cardiac valve.

Figure 4C:
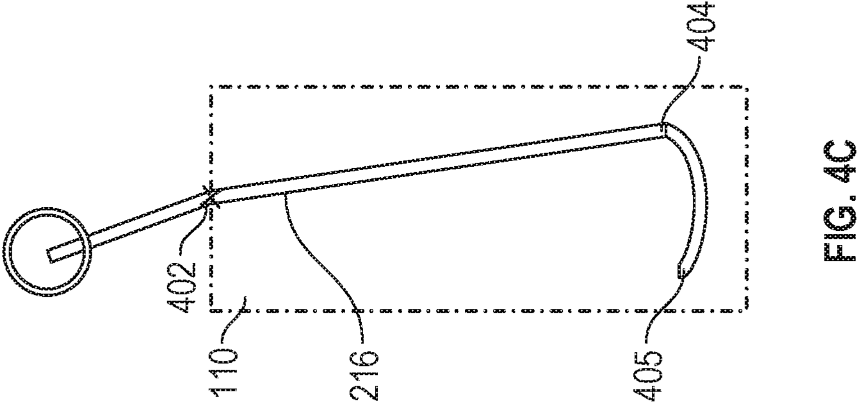
FIGS. 4A to 4C illustrate an alternative exemplary stent configuration providing the second bend of the heart valve therapeutic device in accordance with the principles of the present disclosure.
Figure 4B:
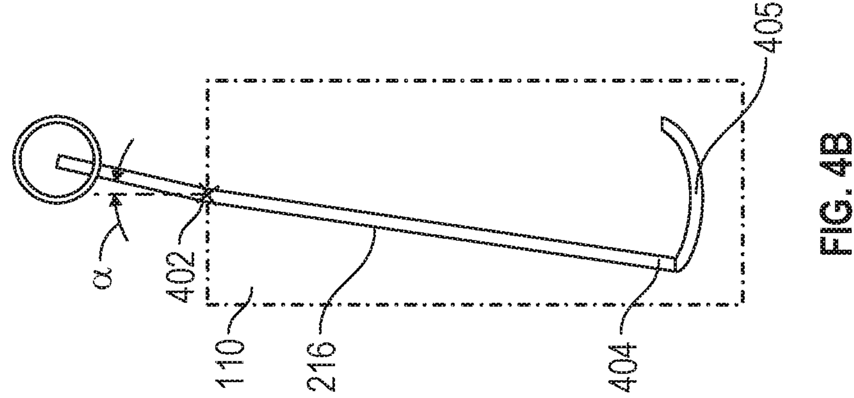
Figure 4A:
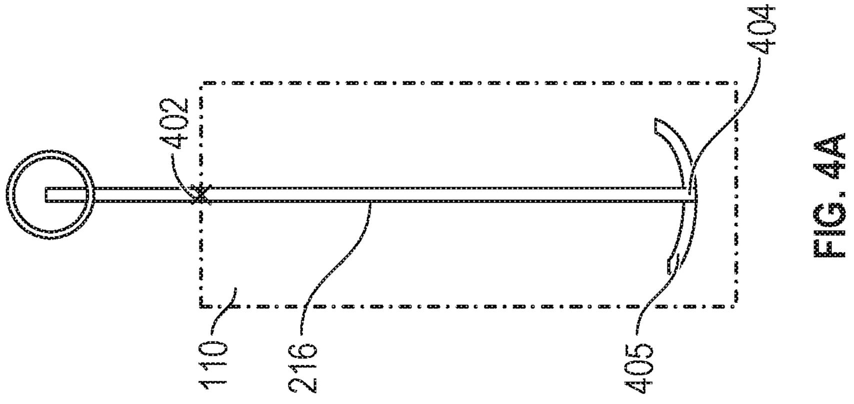
Figure 5B:
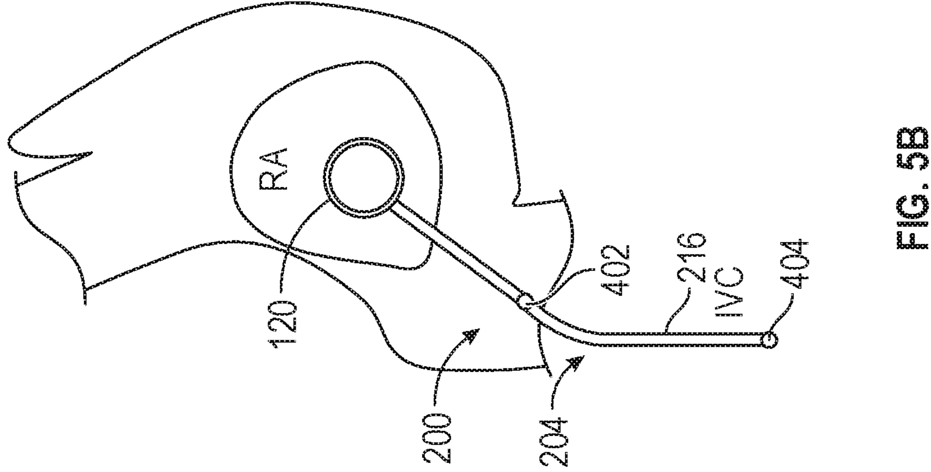
FIGS. 5A and 5B illustrate the adjustment of the second bend of the heart valve therapeutic device using the stent configuration of FIGS. 4A to 4C.
Figure 5A:
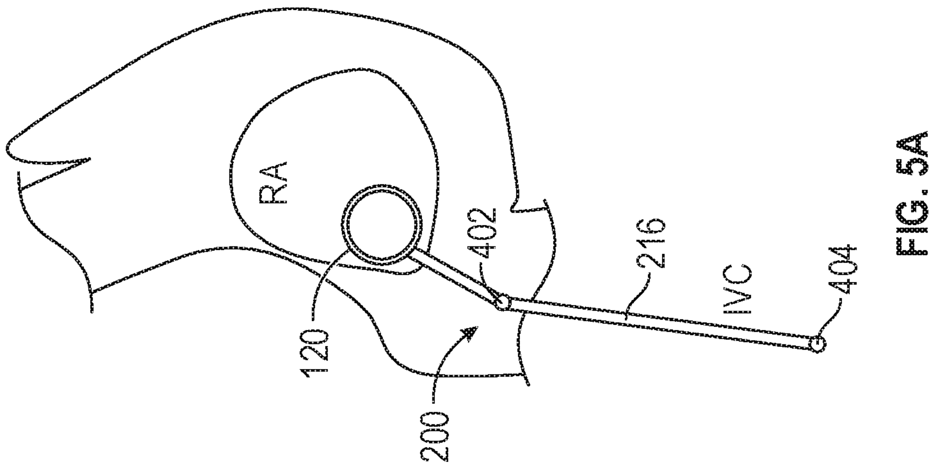

Referring now to FIGS. 4A to 4C, an alternative stent configuration for providing the adjustable second bend of heart valve therapeutic device 100 is provided. In this embodiment, elongated rail 206 may have first preformed bend 202, but does not have second preformed bend 204. Instead, the second adjustable bend, e.g., for navigation of support 200 from the IVC into the RA, may be provided by the stent configuration of FIGS. 4A to 4C, as described in further detail below. As shown in FIGS. 4A to 4C, a first end of anchor tube 216 may be pivotally coupled to anchor 110 at pivot point 402, while an opposing end 404 of anchor tube 216 may slidably coupled to stent 110, e.g., along rail 405. Accordingly, anchor tube 216 may be actuated, e.g., via handle 900, to move end 404 of anchor tube 216 along rail 405 such that anchor tube 216 pivots about pivot point 402. As shown in FIG. 4B, anchor tube 216 may be pivoted about pivot point 402 to provide support 200 a second bend angle of a. As shown in FIGS. 5A and 5B, by moving end 404 of anchor tube 216 relative to pivot point 402, the angle of second adjustable bend 204 may be selectively adjusted to facilitate navigation of support 200 through the IVC and right atrium RA.

Figure 6C:
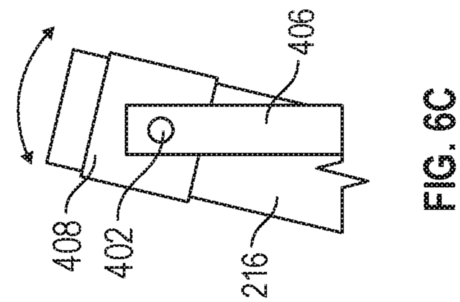
FIGS. 6A to 6C illustrate the pivot point of the stent configuration of FIGS. 4A to 4C.
Figure 6B:
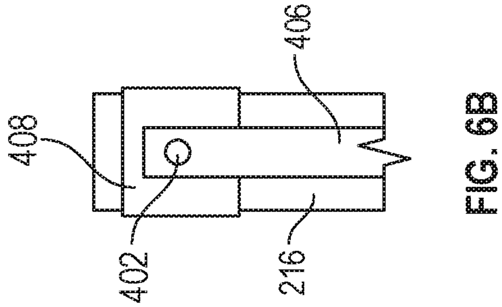
Figure 6A:
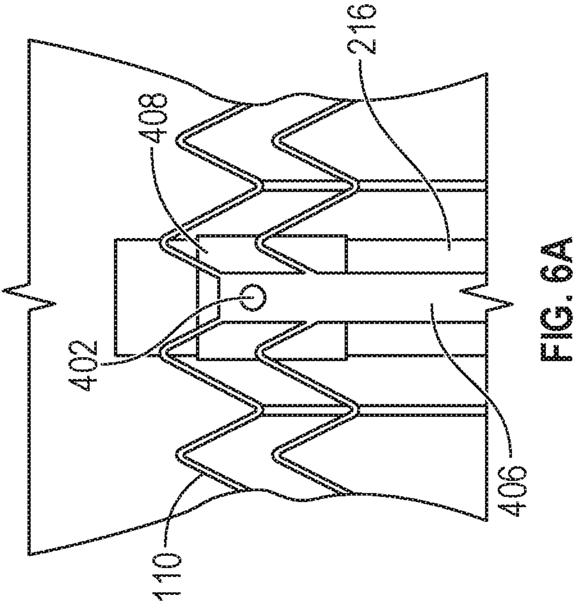
Figure 7A:
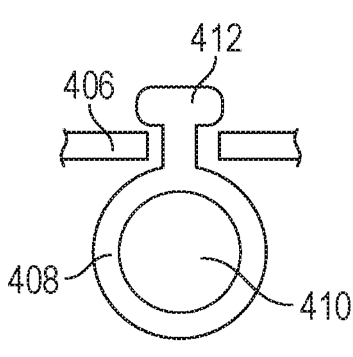
FIGS. 7A to 7C illustrate an exemplary collar of the stent configuration of FIGS. 6A to 6C constructed in accordance with the principles of the present disclosure.
Figure 7B:
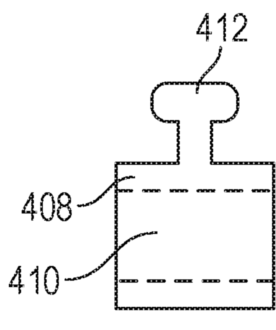
Figure 7C:
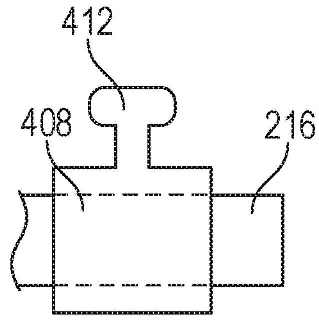

As shown in FIGS. 6A to 6C, anchor tube 216 may be pivotally coupled to spine 406 of anchor 110 at pivot point 402 via collar 408. Collar 408 is sized and shaped to receive and secure anchor tube 216 to pivot point 402. For example, as shown in FIGS. 7A to 7B, collar 408 may include lumen 410 sized and shaped to receive anchor tube 216 therethrough. Collar 408 may then be fixed to anchor tube 216 by, e.g., welding or an adhesive. In addition, collar 408 further may include tab 412 for rotatably engaging with spine 406 of anchor 110 at pivot point 402. Accordingly, tab 412 may extend from collar 408 via a neck portion sized and shaped to fit through an opening within spine 406, while providing adequate space such that collar 408 may rotate relative to spine 406. Tab 412 may have a larger diameter than the opening of spine 406, thereby preventing dislodgment of collar 408 from spine 406.

Figure 8A:
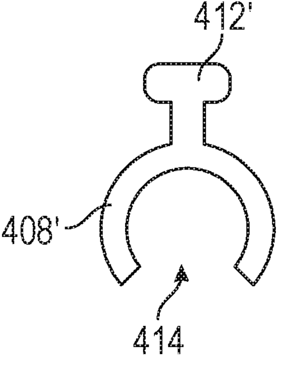
FIGS. 8A and 8B illustrate an alternative exemplary collar of the stent configuration of FIGS. 6A to 6C constructed in accordance with the principles of the present disclosure.
Figure 8B:
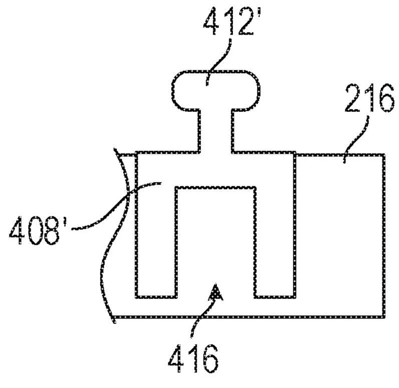
Figures 9A, 9B:
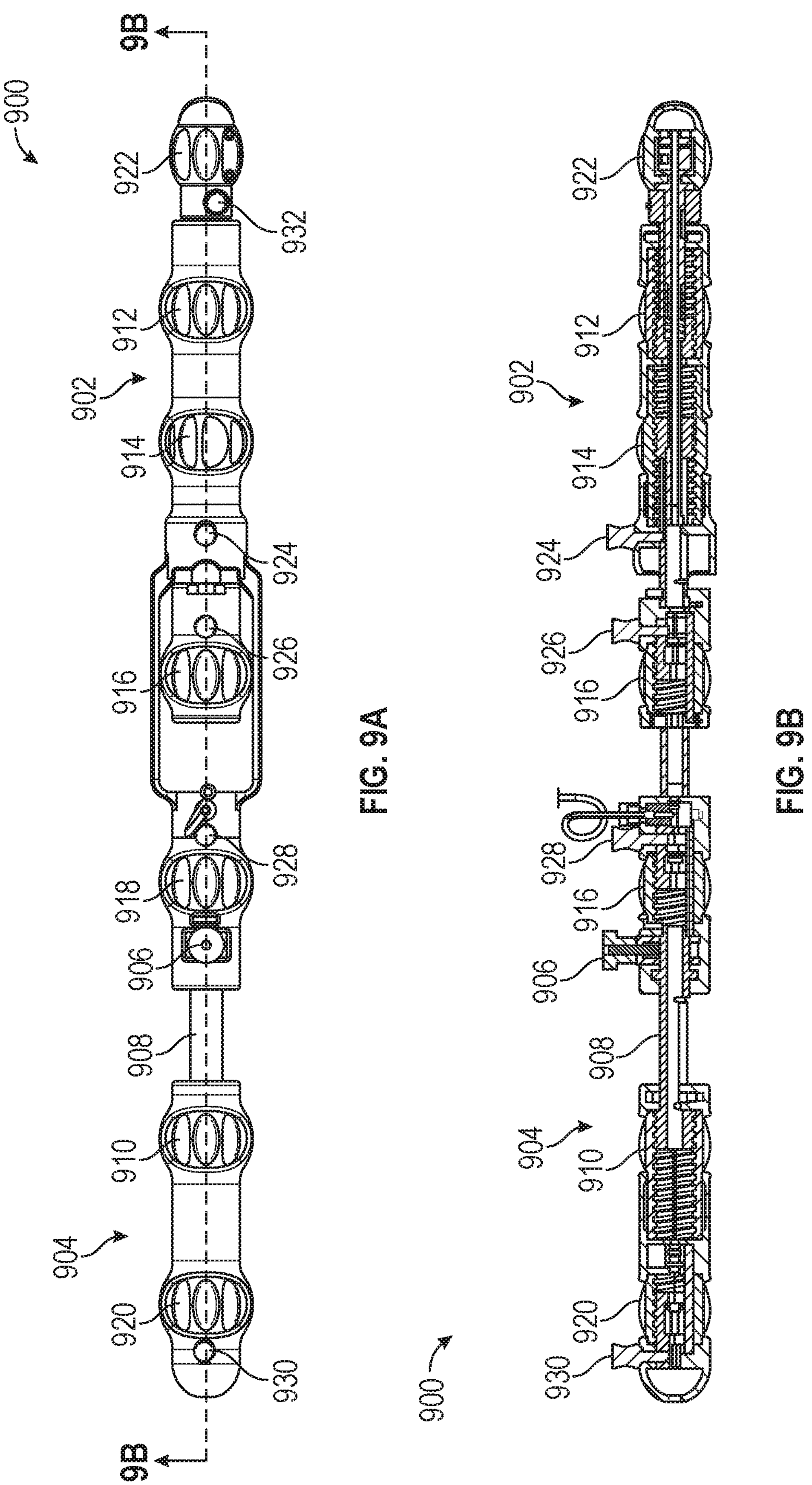
FIGS. 9A to 9D illustrate an exemplary handle of the heart valve therapeutic device of FIG. 1 constructed in accordance with the principles of the present disclosure.
Figure 9C:
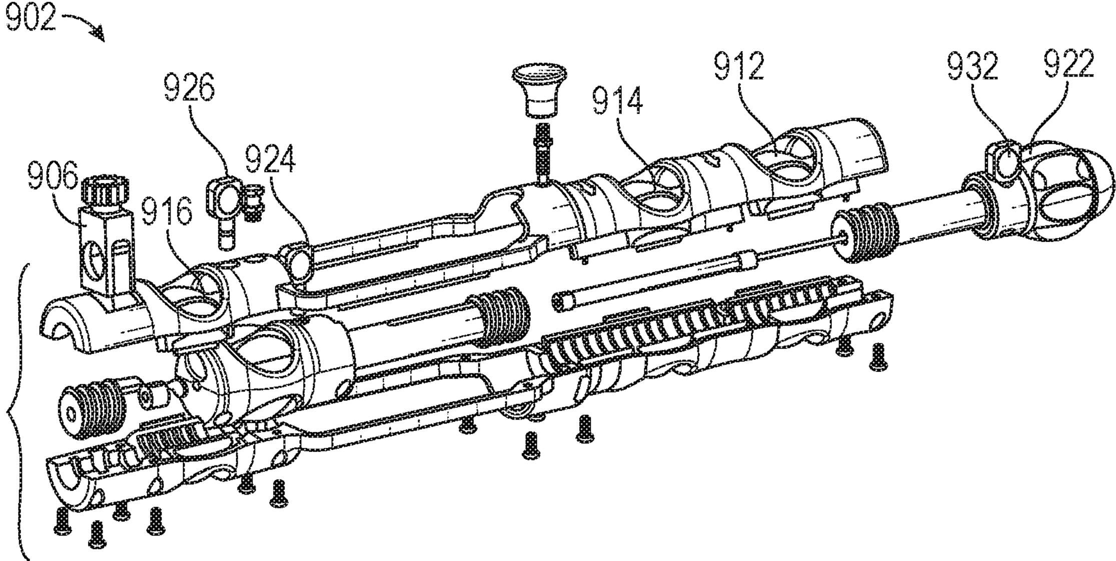
Figure 9D:
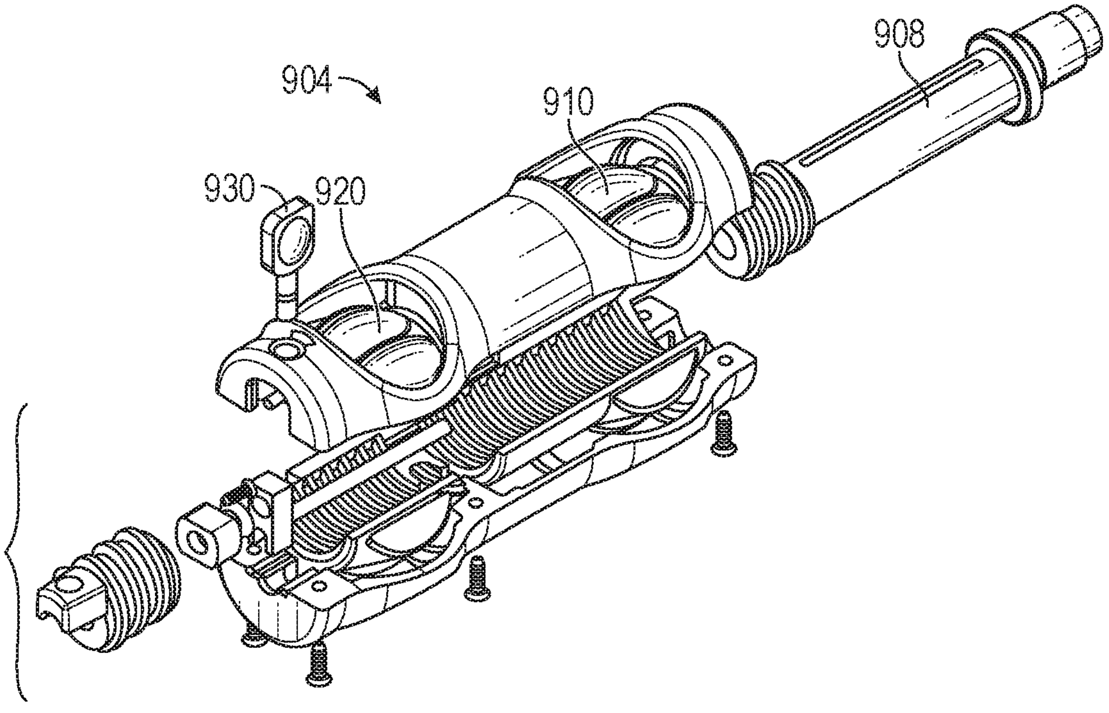

FIGS. 8A and 8B illustrate alternative collar 408' for pivotally coupling anchor tube 408 with spine 406 of anchor 110. Collar 408' may be constructed similar to collar 408, except that, as shown in FIG. 8A, collar 408' may include opening 414 extending longitudinally along the bottom portion of collar 408'. Accordingly, collar 408' may receive anchor tube 216 via opening 414, e.g., via a snap fit connection. For example, collar 408' may expand radially outwardly as anchor tube 216 is pushed through opening 414. As shown in FIG. 8B, collar 408' further may include opening 416, which may facilitate coupling of collar 408' and anchor tube 216. Collar 408' may then be fixed to anchor tube 216 by, e.g., welding or an adhesive.

Referring now to FIGS. 9A to 9D, exemplary actuator 900 is provided. Actuator 900 may include proximal portion 902 rotatably coupled to distal portion 904, e.g., via rod 908. Actuator 900 may include tab 906, which may be moved between a locked position where proximal portion 902 is prevented from rotating relative to distal portion 904, and an unlocked positioned where proximal portion 902 may be rotated relative to distal portion 904, to thereby rotate prosthetic device 120, as described in further detail below.

Moreover, actuator 900 includes a plurality of interfaces, e.g., interfaces 910, 912, 914, 916, 918, 920, 922, for adjusting the position of prosthetic device 120 and support 200 relative to the patient's native cardiac valve, adjusting the bending angles of the first and second adjustable bends of elongated rail 206, locking the distal, implantable portion of support 200, and detaching the distal, implantable portion of support 200 from the proximal, delivery portion of support 200 to thereby implant the distal, implantable portion of support 200. For example, interfaces 910, 912 may be operatively coupled to support 200 and actuated to adjust the position of prosthetic device 120 and support 200 relative to the patient's native cardiac valve, and interface 914 may be operatively coupled to support 200 and actuated to adjust the bending angles of the first and second adjustable bends of elongated rail 206, as described in further detail below. Moreover, interfaces 916, 918 may be operatively coupled to support 200 and actuated to lock the distal, implantable portion of support 200 to each other, and interfaces 920, 922 may be operatively coupled to support 200 and actuated to detach the distal, implantable portion of support 200 from the proximal, delivery portion of support 200 to thereby implant the distal, implantable portion of support 200, as described in further detail below.

The interfaces of actuator 900 may be, e.g., rotatable knobs, buttons, sliders, or the like, which may be manipulated by a clinician. The interfaces of actuator 900 may be coupled to an internal lead screw, each lead screw connected to a collar rigidly attached to a select component of support 200, such that actuation of a given interface actuates a particular component of support 200. Actuator 900 further may include safety pins 924, 926, 928, 930, 932, which may initially be in an engaged positioned whereby the safety pins are coupled to actuator 900, thereby prevent actuation of a respective interface. For example, safety pins 924, 926, 928, 930, 932 may be associated with interfaces 914, 916, 918, 920, 922, respectively. The safety pins may be removed from actuator 900, e.g., by pulling them, by a clinician, and returned to the engaged position after actuation of the respective interface. In another embodiment the actuators may be replaced by alternative mechanism for controlling linear actuation, e.g. lever, thumbwheel, and/or linear slider.

Figure 10A:
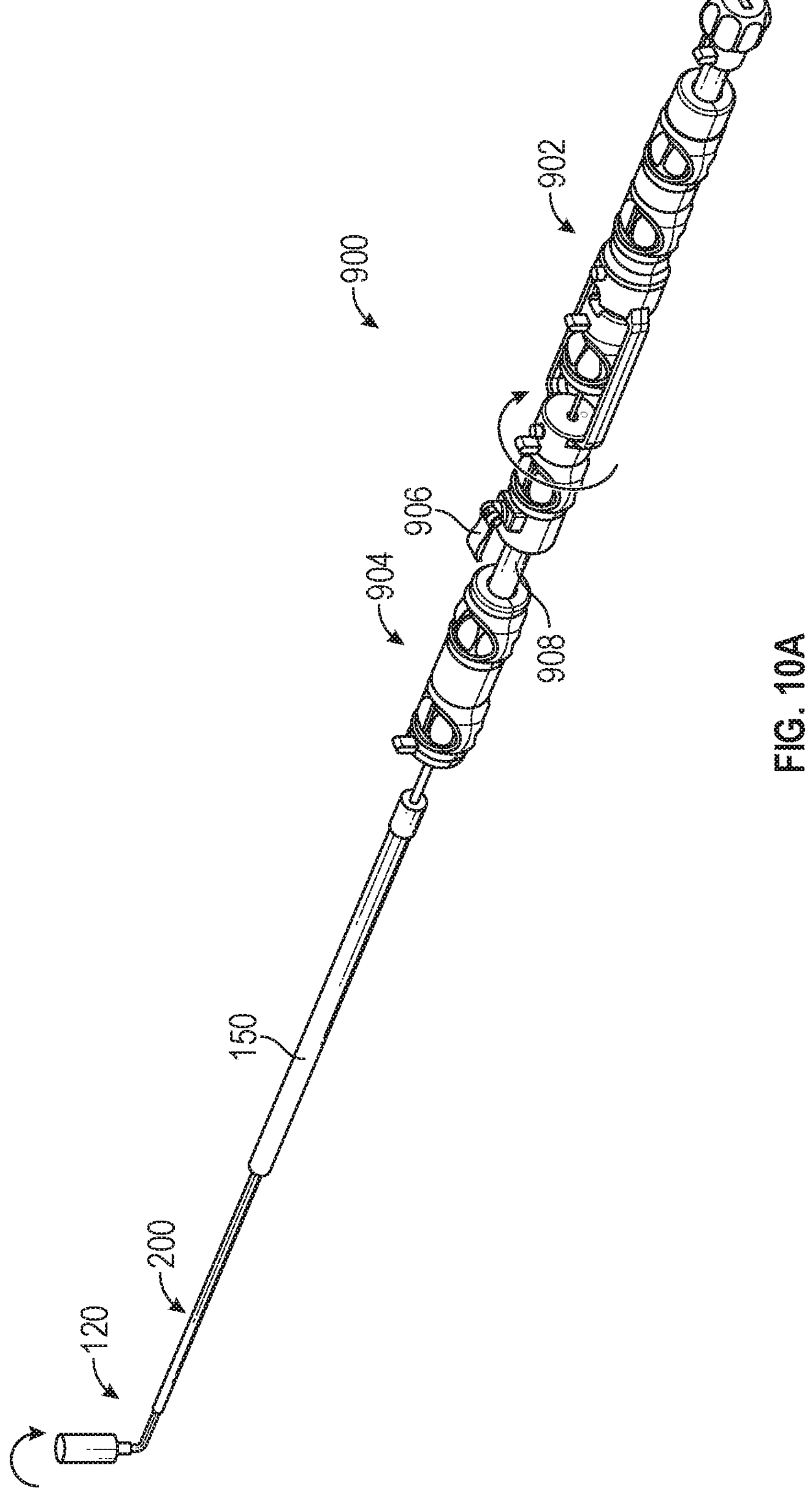
FIGS. 10A to 10D illustrate positional adjustment of the distal end of the heart valve therapeutic device using the handle of FIGS. 9A to 9D in accordance with the principles of the present disclosure.

Referring now to FIGS. 10A to 10D, positional adjustment of the distal end of the heart valve therapeutic device 100, e.g., via support 200, using actuator 900 is described. As shown in FIG. 10A, tab 906 may be transitioned from the locked positioned to the unlocked positioned, e.g., by flipping tab 906. When tab 906 is in the unlocked position, proximal portion 902 of actuator 900 may be rotated relative to distal portion 904 of actuator 900. Proximal portion 902 may be coupled to elongated rail 206, such that rotation of proximal portion 902 causes elongated rail 206, and accordingly prosthetic device 120 coupled thereto, to rotate relative to the longitudinal axis of support 200. Accordingly, the clinician may hold distal portion 904 fixed relative to the patient, while rotating proximal portion 902 to adjust the rotational position of prosthetic device 120.

Figure 10B:
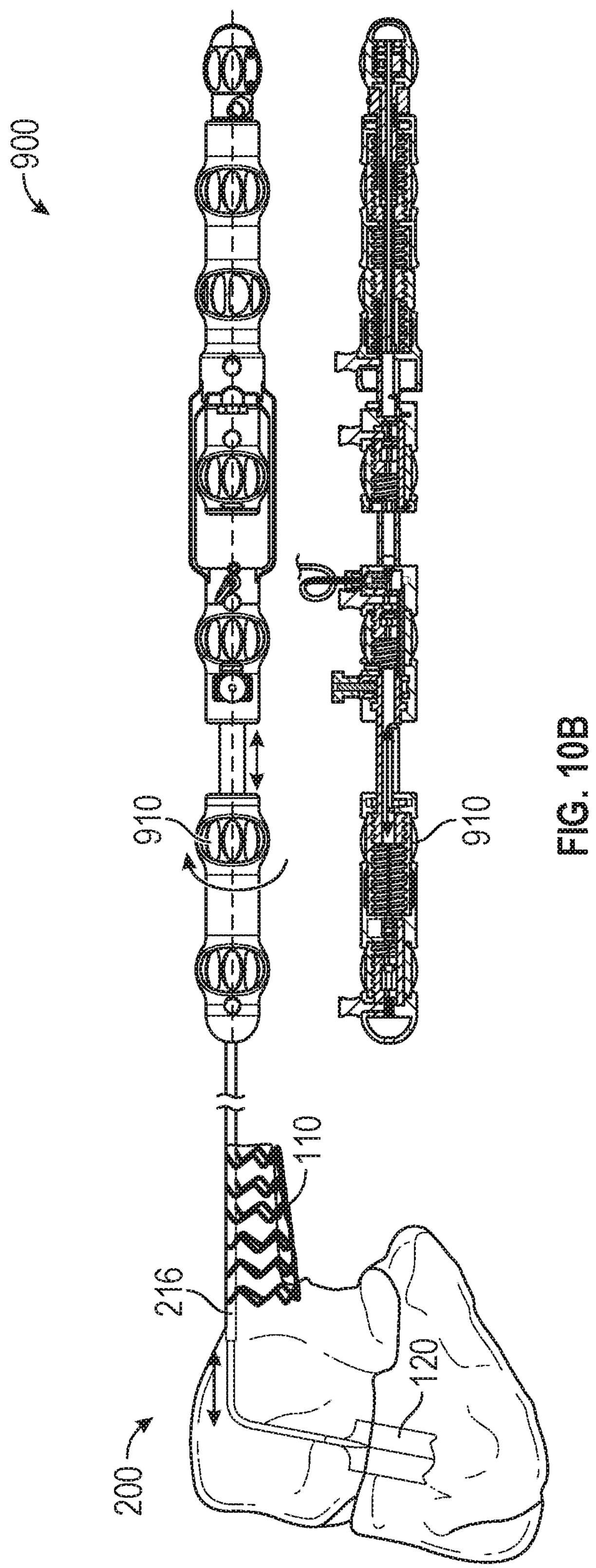

As shown in FIG. 10B, interface 910 of actuator 900 may be actuated to adjust the length of support 200, to thereby adjust the axial location of the one or more adjustable bends of elongated rail 206 relative to actuator 900. For example, actuation of interface 910 may cause the internal lead screw coupled thereto to rotate to thereby cause proximal portion 902 to move axially relative to distal portion 904. As proximal portion 902 is coupled to elongated rail 206 as described above, axially movement of proximal portion 902 relative to distal portion 904 while distal portion 904 is held fixed relative to the patient by the clinician, will cause elongated rail 206 to extend axially along the longitudinal axis of support 200. Thus, the axial distance of the adjustable bends of elongated rail 206 from actuator 900 may be shortened or lengthen via interface 910. The actuator may include a locking mechanism to limit the axial movement of distal portion 904 relative to proximal portion 902, as described in further detail below with regard to FIGS. 18A to 20.

Figure 10C:
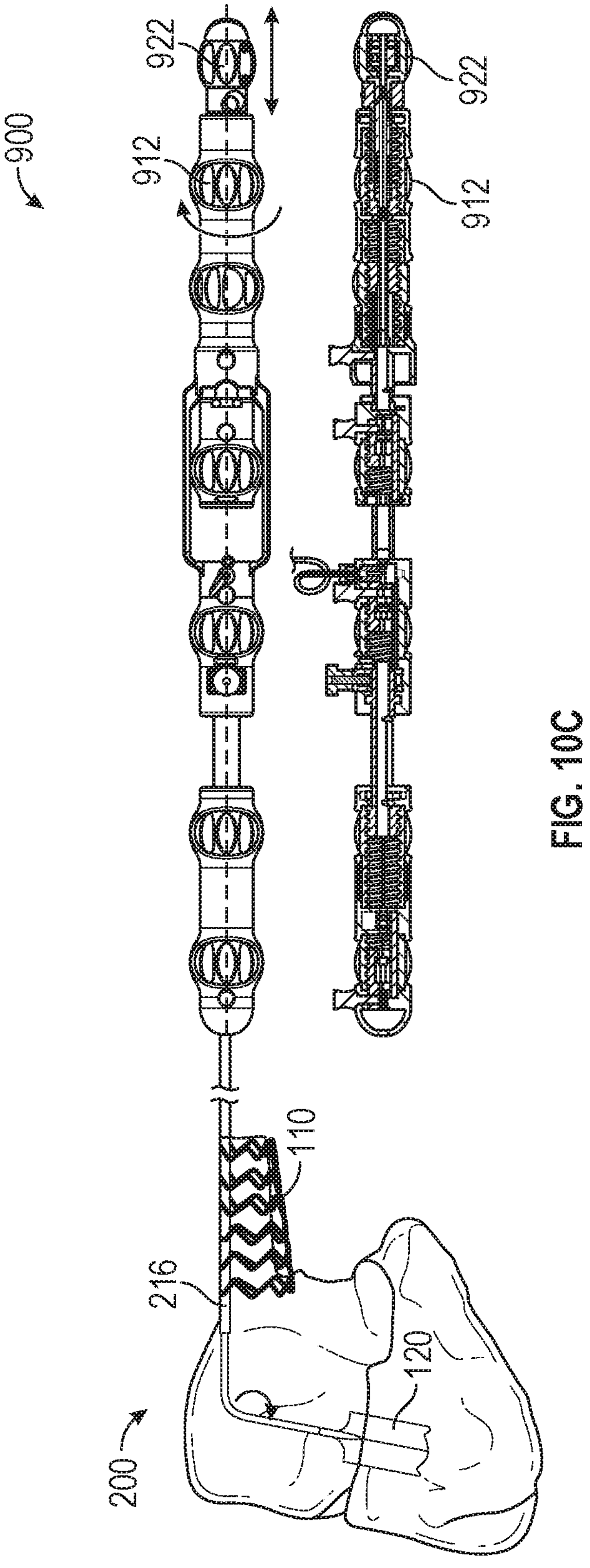

As shown in FIG. 10C, interface 912 of actuator 900 may be actuated to adjust the angle of an adjustable preformed bend, e.g., first preformed bend 202, of elongated rail 206. For example, actuation of interface 912 may cause the internal lead screw coupled thereto to rotate to thereby cause elongated rail 206 to move axially relative to first shaping catheter 208. As described above, because first shaping catheter 208 is more stiff than first preformed bend 202 of elongated rail 206, axial movement of first shaping catheter 208 relative to first preformed bend 202 will adjust the angle of first preformed bend 202. As will be understood by a person having ordinary skill in the art, first shaping catheter 208 may be actuated via an interface of actuator 900 while elongated rail 206 remains stationary relative to the patient, such that axial movement of first shaping catheter 208 relative to first preformed bend 202 adjusts the angle of first preformed bend 202. Similarly, second shaping catheter 210 may be actuated via an interface of actuator 900 while elongated rail 206 remains stationary relative to the patient, such that axial movement of second shaping catheter 210 relative to second preformed bend 204 adjusts the angle of second preformed bend 204. Actuator 900 may have any number of interfaces required to adjust any respective number of preformed bends of elongated rail 900, as described above.

Figure 10D:
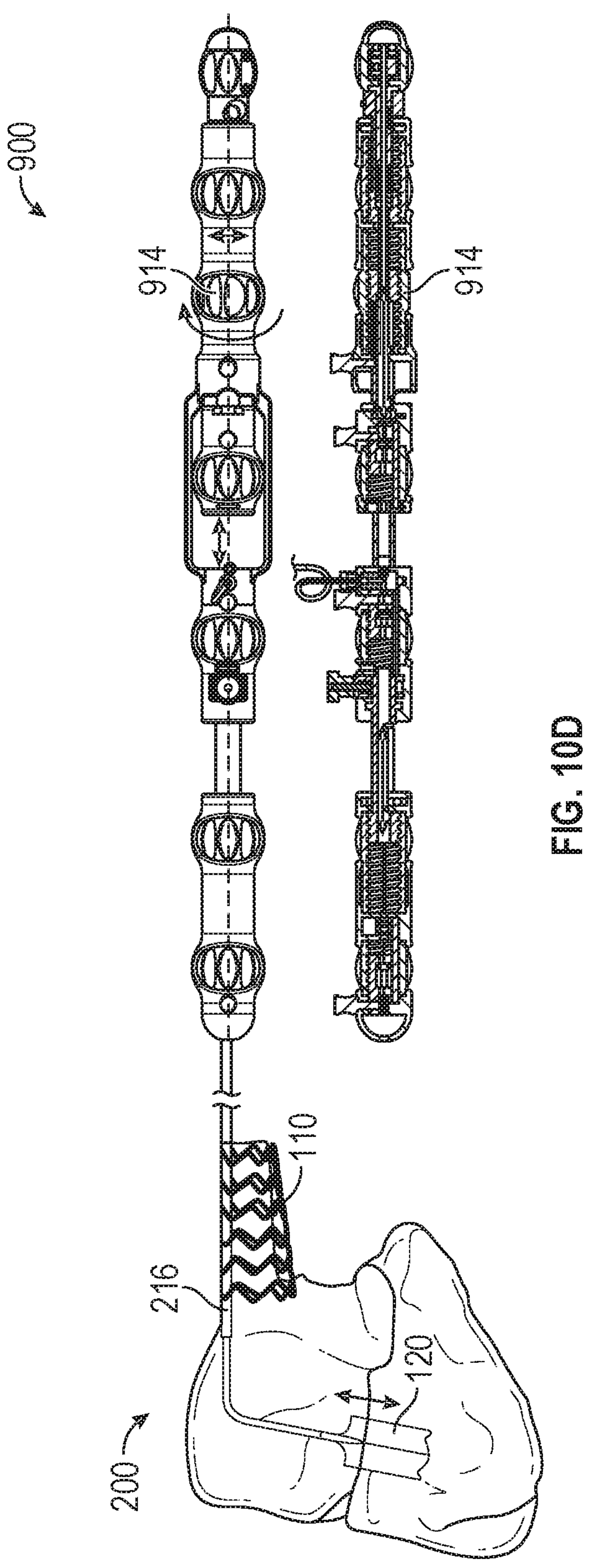

As shown in FIG. 10D, interface 914 of actuator 900 may be actuated to adjust the depth of prosthetic device 120 relative to the patient's native cardiac valve, e.g., toward the patient's right atrium or toward the patient's right ventricle. For example, actuation of interface 914 may cause the internal lead screw coupled thereto to rotate to thereby cause body support catheter 212 to move axially relative to actuator 900. As body support catheter 212 is coupled to prosthetic device 120, e.g., via connector 214, axial movement of body support catheter 212 will adjust the depth of prosthetic device 120 relative to the patient's native cardiac valve.

Figures 11A, 11B:
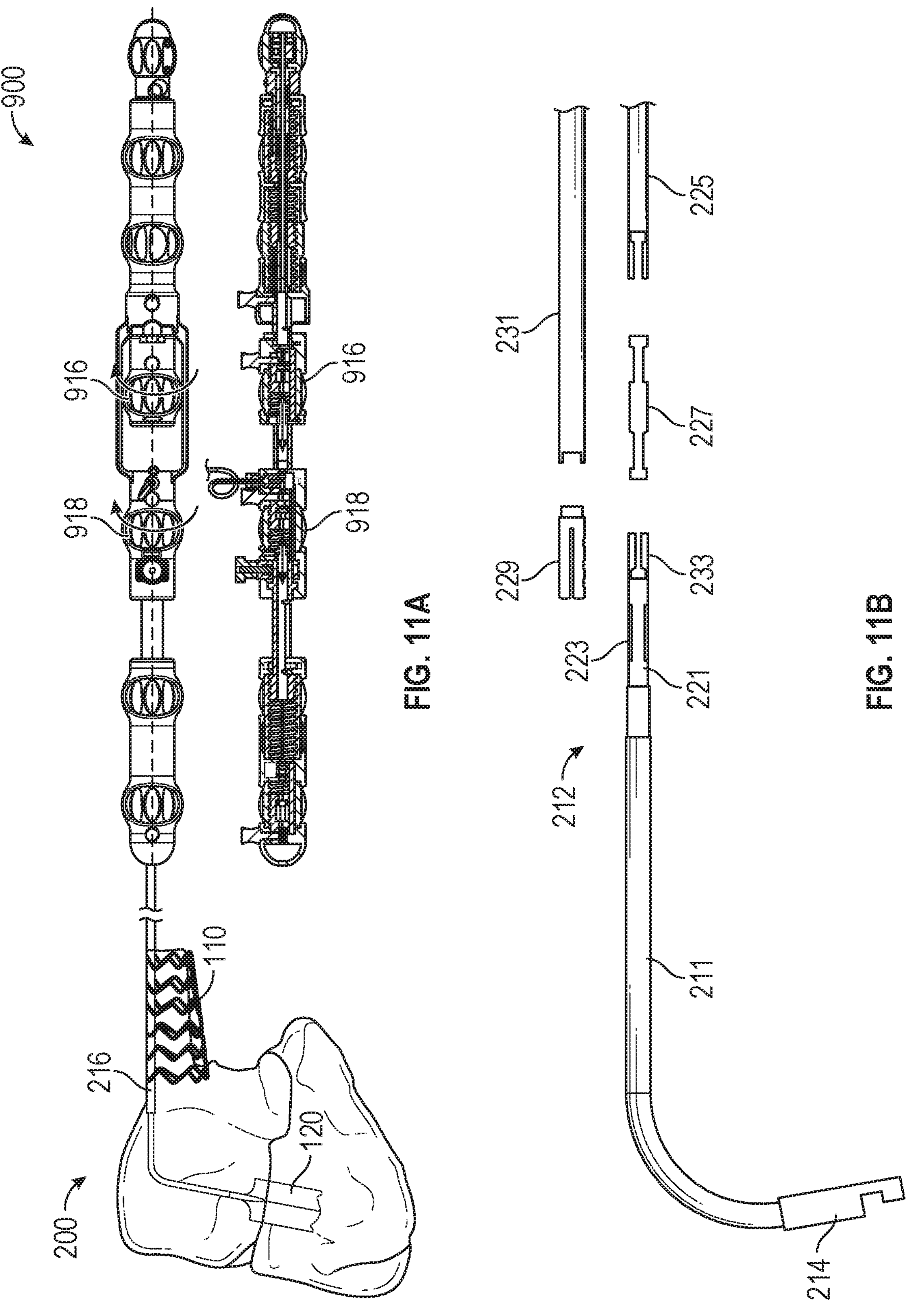
FIGS. 11A and 11B illustrate locking of the distal end of the heart valve therapeutic device using the handle of FIGS. 9A to 9D in accordance with the principles of the present disclosure.

As shown in FIGS. 11A and 11B, interfaces 916, 918 may be actuated to lock the distal, implantable portion of support 200 to each other. Support 200 may include a locking mechanism as described in U.S. Pat. No. 11,219,525 to Vesely, the entire contents of which is incorporated herein by reference. For example, as shown in FIG. 11B, body support catheter 212 may include distal, implantable portion 211 removably detachable to proximal, delivery portion 225 via body support catheter connection 227. Distal, implantable portion 211 may include distal body support locking portion 221 and distal body support connection portion 233. Distal body support locking portion 221 and distal body support connection portion 233 have a lumen sized and shaped to receive second shaping catheter 210, and accordingly first shaping catheter 208 and elongated rail 206, therethrough.

Distal body support locking portion 221 may include one or more slits, e.g., a U-shaped slit, forming interference locking portion 223. Interference locking portion 223 may be a wedged portion that has a thickness that is greater than the thickness of distal body support locking portion 221 and distal body support connection portion 233, such that the wedged portion may be pushed radially inward to lock distal, implantable portion 211 to second shaping catheter 210, as described in further detail below. Distal body support connection portion 233 may include an opening, e.g., a T-shaped opening, sized and shaped to interlink with body support catheter connection 227.

Body support catheter connection 227 may include a distal interlinking portion sized and shaped to releasably engage with distal body support connection portion 233 of distal, implantable portion 211, and a proximal interlinking portion sized and shaped to engage with proximal, delivery portion 225. For example, the distal interlinking portion of body support catheter connection 227 may have a shape that corresponds with the shape of the opening of distal body support connection portion 233, such that when the distal body support interlinking portion of body support catheter connection 227 is in its collapsed state, it interlinks with distal body support connection portion 233. The distal interlinking portion of body support catheter connection 227 may be biased radially outward, and may transition from the expanded state to a collapsed state upon application of a radially inward force. Accordingly, body support catheter lock 229 may be slidably disposed over body support catheter 212, such that when body support catheter lock 229 is disposed over the distal interlinking portion of body support catheter connection 227 and distal body support connection portion 233, body support catheter connection 227 remains engaged with distal body support connection portion 233.

Body support catheter lock 229 may include a proximal portion having a geometry sized and shaped to engage with the distal end of body support catheter pusher 231. Both body support catheter lock 229 and body support catheter pusher 231 have a lumen sized and shaped to slidably receive body support catheter 212 therethrough. Accordingly, body support catheter pusher 231 may be advanced distally responsive to actuation at actuator 900, e.g., by actuating interface 918 actuator 900 in a first direction as shown in FIG. 11A, such that body support catheter pusher 231 engages with body support catheter lock 229 to push body support catheter lock 229 distally from over body support catheter connection 227 to over distal body support locking portion 223. When body support catheter lock 229 is disposed over distal body support locking portion 223, the wedge shape of distal body support locking portion 223 causes distal body support locking portion 223 to move radially inward and engage with the outer surface of second shaping catheter 210 to thereby to lock distal, implantable portion 211 to second shaping catheter 210.

Body support catheter lock 229 may include one or more longitudinal slits which may permit the distal portion of body support catheter lock 229 to expand radially as body support catheter lock 229 is pushed over the wedge shape of distal body support locking portion 223 of distal locking portion 221. As body support catheter lock 229 expands radially, it engages with the inner surface of the lumen of anchor tube 216 to thereby lock distal, implantable portion 211 to anchor tube 216. Interface 918 may then be actuated in the opposite direction, such that body support catheter pusher 231 is retracted proximally relative to distal, implantable portion 211 to thereby expose the distal body support interlinking portion of body support catheter connection 227. Upon exposure from body support catheter pusher 231, the distal body support interlinking portion of body support catheter connection 227 transitions to the expanded state and disengages with distal body support connection portion 233. Proximal, delivery portion 225 of body support catheter 212 may then be removed from the patient while distal, implantable portion 211 of body support catheter 212 remains implanted. Similarly, interface 916 of actuator 900 may be actuated to move a corresponding pusher to lock and disconnect additional distal, implantable portions of support 200 to each other. As will be understood by a person having ordinary skill in the art, actuator 900 may include any number of interfaces to lock a corresponding number of distal, implantable portions of support 200.

Figure 12A:
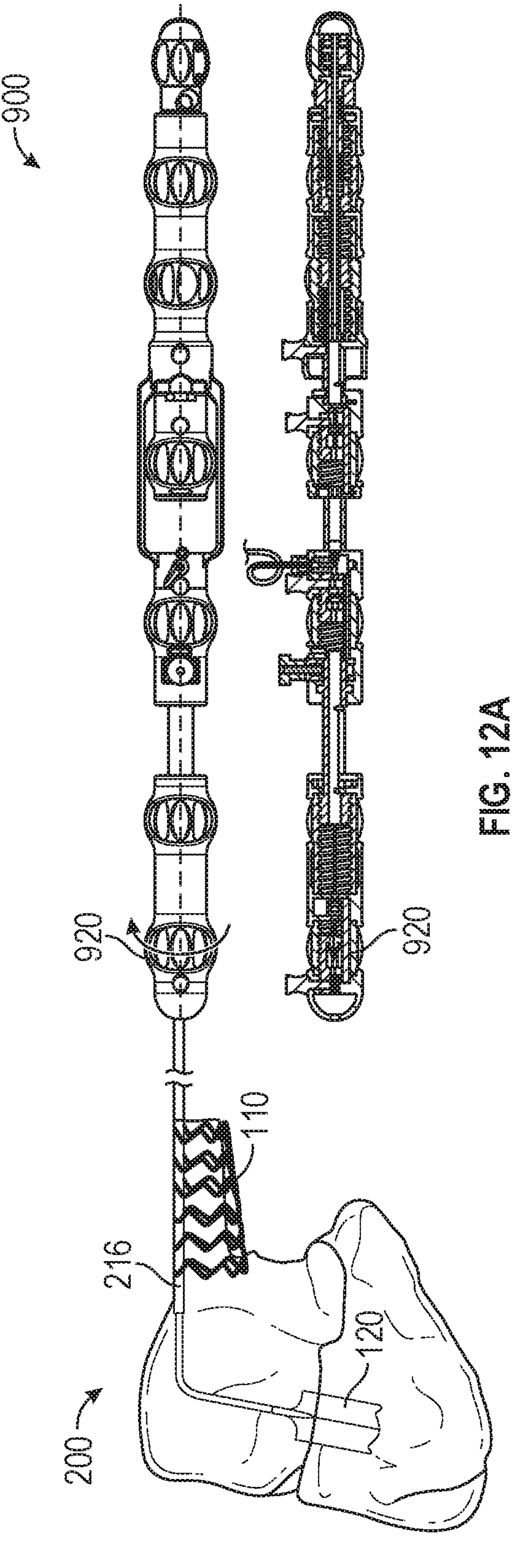
FIGS. 12A and 12B illustrate detachment of the distal end of the body support catheter of the heart valve therapeutic device using the handle of FIGS. 9A to 9D in accordance with the principles of the present disclosure.
Figure 12B:
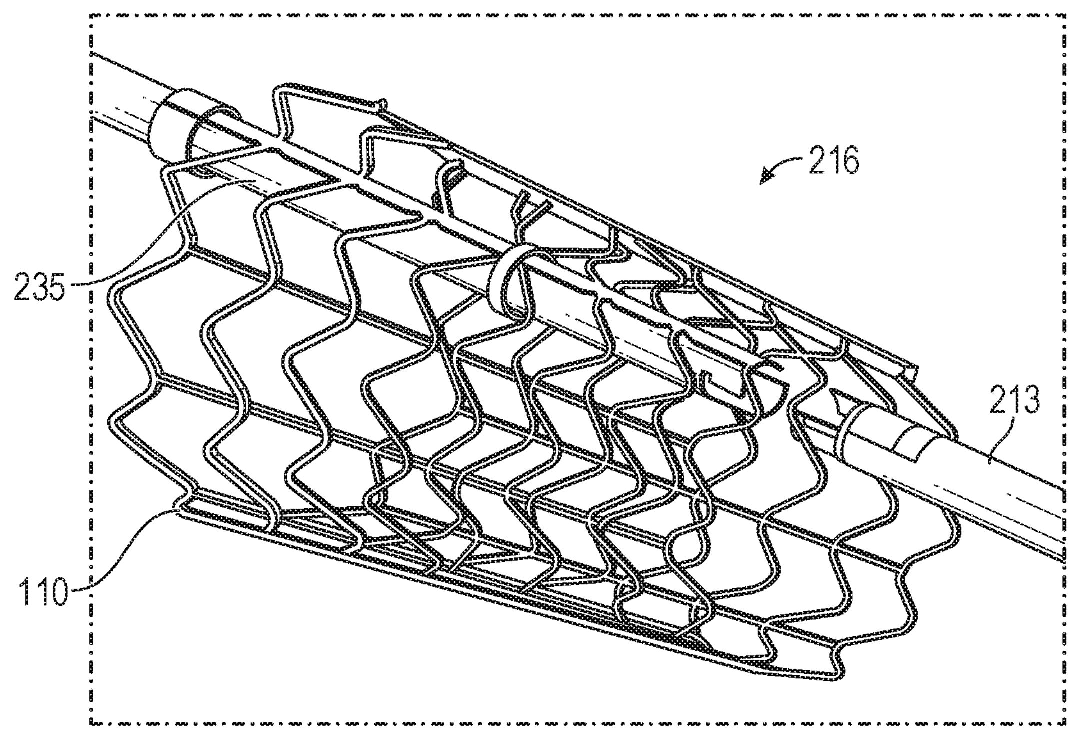

Referring now to FIGS. 12A and 12B, interface 920 of actuator 900 may be actuated to detach proximal, delivery portion 213 of anchor tube 216 from distal, implantable portion 235 of anchor tube 216. For example, proximal, delivery portion 213 may be retracted proximally responsive to actuation of actuator 900, e.g., by actuating interface 920 of actuator 900, to expose the distal anchor tube interlinking portion of the anchor tube connection. The distal anchor tube interlinking portion may self-expand from a collapsed delivery state within proximal, delivery portion 213 to an expanded state upon exposure from proximal, delivery portion 213, such that the distal anchor tube interlinking portion disengages with distal, implantable portion 235. As shown FIG. 12B, proximal, delivery portion 213 along with the other proximal, delivery components of support 200 may be removed from the patient while distal, implantable portion 235 remains implanted within the patient.

Figures 13A, 13B:
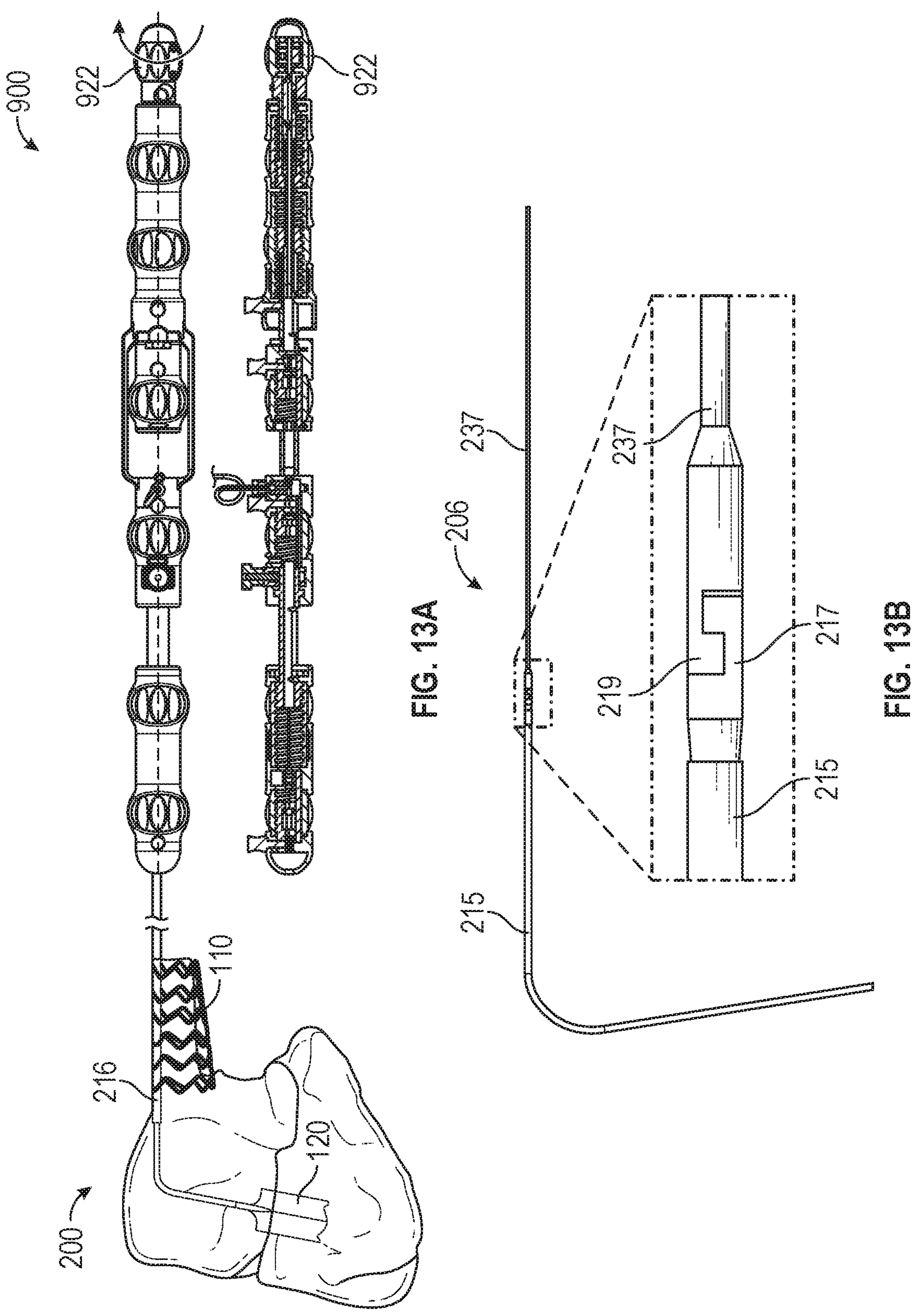
FIGS. 13A to 13C illustrate detachment of the distal end of the elongated rail of the heart valve therapeutic device using the handle of FIGS. 9A to 9D in accordance with the principles of the present disclosure.
Figure 13C:
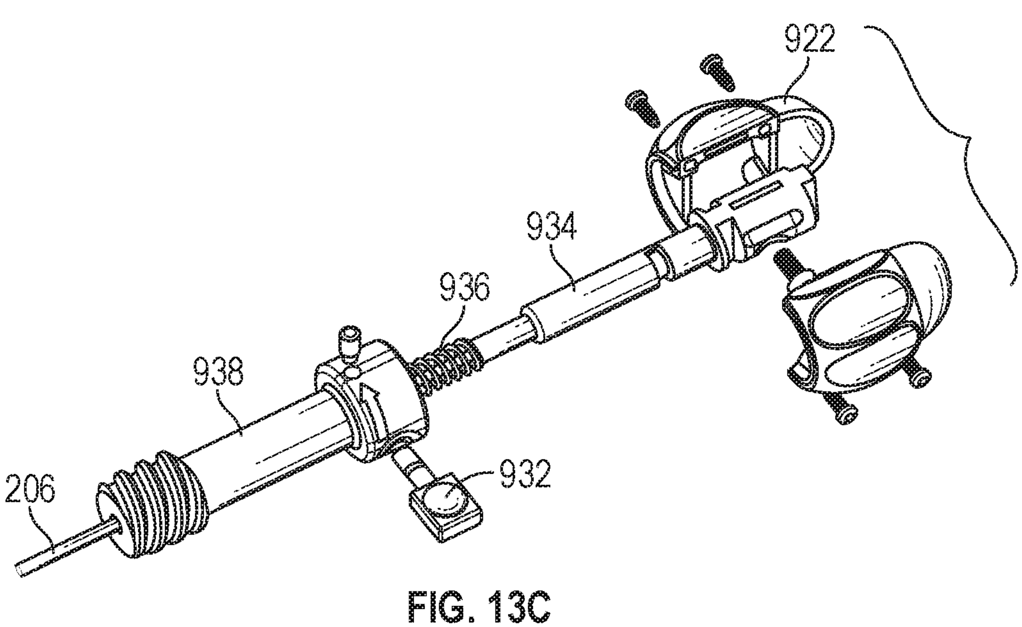

Referring now to FIGS. 13A to 13C, interface 922 of actuator 900 may be actuated to detach proximal, delivery portion 237 of elongated rail 206 from distal, implantable portion 215 of elongated rail 206. As shown in FIG. 13B, distal, implantable portion 215 and proximal, delivery portion 237 may be removably attached together. For example, distal, implantable portion 215 may have first geometry 217, and proximal, delivery portion 237 may have second geometry 219 corresponding to first geometry 217 such that distal, implantable portion 215 may engage with proximal, delivery portion 237 during delivery. For example, first and second geometries 217, 219 may be notches and teeth, wherein a tooth of first geometry 217 fits in the notch of second geometry 219 and a tooth of second geometry 219 fits in the notch of first geometry 217, thereby attaching elongated rail 206 during delivery. Distal, implantable portion 215 may be disengaged from proximal, delivery portion 237 for implantation of proximal, delivery portion 237 responsive to actuation of actuator 900, e.g., by actuating interface 922 of actuator 900.

As shown in FIG. 13C, interface 922 may be coupled to internal housing 934, which is fixed elongated rail 206 extending through lead screw 938 having safety pin 932. Interface 922 may be rotated upon removal of pin 932 by the clinician. Accordingly, rotation of interface 922 causes internal housing 934 and elongated rail 206 to rotate relative to prosthetic device 120. As internal housing 934 and elongated rail 206 rotates to disengage proximal, delivery portion 237 of elongated rail 206 from distal, implantable portion 215 of elongated rail 206, spring 936 positioned between lead screw 938 and internal housing 934 simultaneously pushes internal housing 934 and interface 922 proximally, thereby releasing proximal, delivery portion 237 from distal, implantable portion 215.

Figure 14:
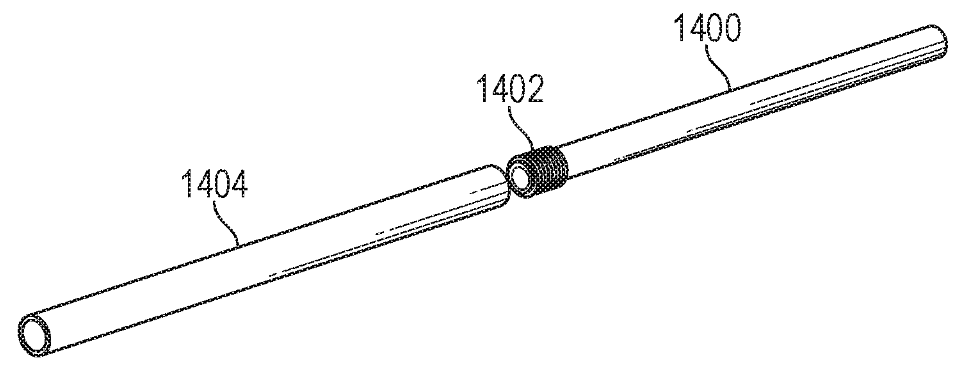
FIG. 14 illustrates an exemplary connection between a body support catheter and a valve spine constructed in accordance with the principles of the present disclosure.

Referring now to FIG. 14, an exemplary connector for coupling a body support catheter and a valve spine is provided. As described above, the distal end of the body support catheter may be coupled to prosthetic device 120, e.g., at a connector, such that elongated rail 206 may extend concentrically through the connector, and the body support catheter may be used to deliver and adjust and finally stabilize the position of prosthetic device 120 across the native cardiac valve. As described in U.S. Pat. No. 11,219,525 to Vesely, the entire contents of which are incorporated herein by reference, the prosthetic device may include a valve spine slidably disposed over the elongated rail, such that the body support catheter is coupled to the prosthetic device via the valve spine.

As shown in FIG. 14, valve spine 1400 may include a plurality of ridges 1402, e.g., a plurality of barbs, disposed at a proximal region of valve spine 1400. For example ridges 1402 may extend circumferentially around an outer surface of proximal region of valve spine 1400. At least the distal region of body support catheter 1404 may be formed of a material that is configured to expand responsive to an external stimulus. For example, the distal region of body support catheter 1404 may be formed of a polymer that is configured to swell when immersed in a dedicated swelling fluid. Accordingly, upon interaction with the external stimulus, the diameter of the distal region of body support catheter 1404 may increase in size, such that the distal region of body support catheter 1404 may be advanced over ridges 1402 of valve spine 1400. Upon removal of the external stimulus, e.g., evaporation of the swelling fluid, the diameter of the distal region of body support catheter 1404 may return to its unexpanded size over ridges 1402, thereby locking body support catheter 1404 to valve spine 1400 via an interference fit between an inner surface of the distal region of body support catheter 1404 and ridges 1402.

Figure 15A:
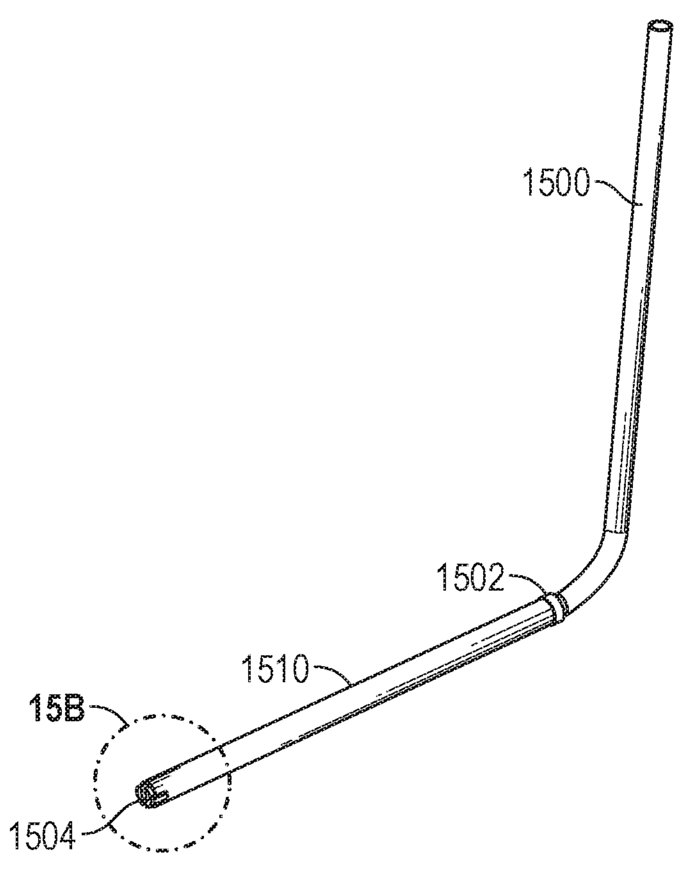
FIGS. 15A and 15B illustrate an alternative exemplary connection between a body support catheter and a valve spine constructed in accordance with the principles of the present disclosure.
Figure 15B:
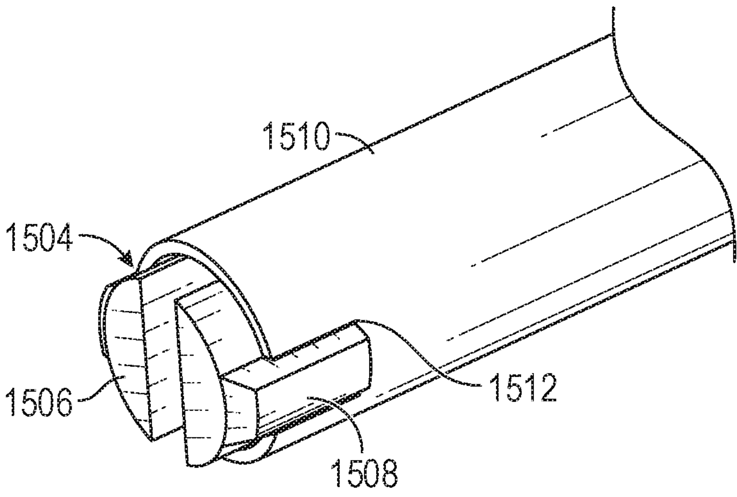

Referring now to FIGS. 15A and 15B, another exemplary connector for coupling a body support catheter and a valve spine is provided. As shown in FIG. 15A, the connector may include elongated rod 1504 having a proximal end coupled to a distal end of body support catheter 1500, e.g., adjacent to proximal abutment 1502 of support 1500. Proximal abutment 1502 may have an outer diameter that is larger than the outer diameter of elongated rod 1504. As shown in FIG. 15B, the distal end of elongated rod 1504 may include one or more collapsible prongs, e.g., pair of prongs 1506. Prongs 1506 are configured to be collapsed from an expanded state radially inward to a collapsed state upon application of a force thereon. Accordingly, upon removal of the force, prongs 1506 may return to their expanded state. As shown in FIG. 15B, each of prongs 1506 may include protrusion 1508 extending radially outward therefrom.

Valve spine 1510 of the prosthetic device may have a lumen sized and shaped to slidably receive elongated rod 1504 therein. As shown in FIG. 15B, the distal region of valve spine 1510 may include one or more grooves 1512 sized and shaped to receive protrusions 1508 therein. For example, grooves 1512 may have a geometry corresponding with the geometry of protrusions 1508, such that when protrusions 1508 are disposed within grooves 1512, valve spine 1510 cannot move distally or rotationally relative to elongated rod 1504. Accordingly, prongs 1506 may be collapsed to the collapsed state, such that the proximal end of valve spine 1510 may be advanced over prongs 1506 and along the length of elongated rod 1504 until the proximal end of valve spine 1510 abuts proximal abutment 1502. Valve spine 1510 and elongated rod 1504 may each have a length such that when the proximal end of valve spine 1510 abuts proximal abutment 1502, protrusions 1508 are aligned with grooves 1512 such that prongs 1506 may return to their expanded state and protrusions 1508 are disposed within grooves 1512. Accordingly, protrusions 1508 and proximal abutment 1502 may limit or prevent axial movement of valve spine 1510 relative to elongated rod 1504, while protrusions 1508 limits or prevents rotation of valve spine 1510 relative to elongated rod 1504.

Alternatively, instead of one or more prongs and protrusions at the distal end of the elongated rod, the distal end of the elongated rod may be configured to be coupled to a plug having a distal abutment. Like the proximal abutment, the distal abutment may have an outer diameter that is larger than the outer diameter of the elongated rod. Accordingly, the proximal end of the valve spine may be advanced over the distal end of the elongated rod and along the length of the elongated rod until the proximal end of the valve spine abuts the proximal abutment, and the distal end of the elongated rod is aligned with the distal end of the valve spine. The plug may then be coupled to the distal end of the elongated rod, e.g. via a threaded mating connection, a snap fit connection, or an interference fit connection, such that the distal abutment of the plug and the proximal abutment of the body support catheter sandwich the valve spine therebetween to thereby prevent axial and rotational movement of the valve spine relative to the elongated rod.

Figure 16A:
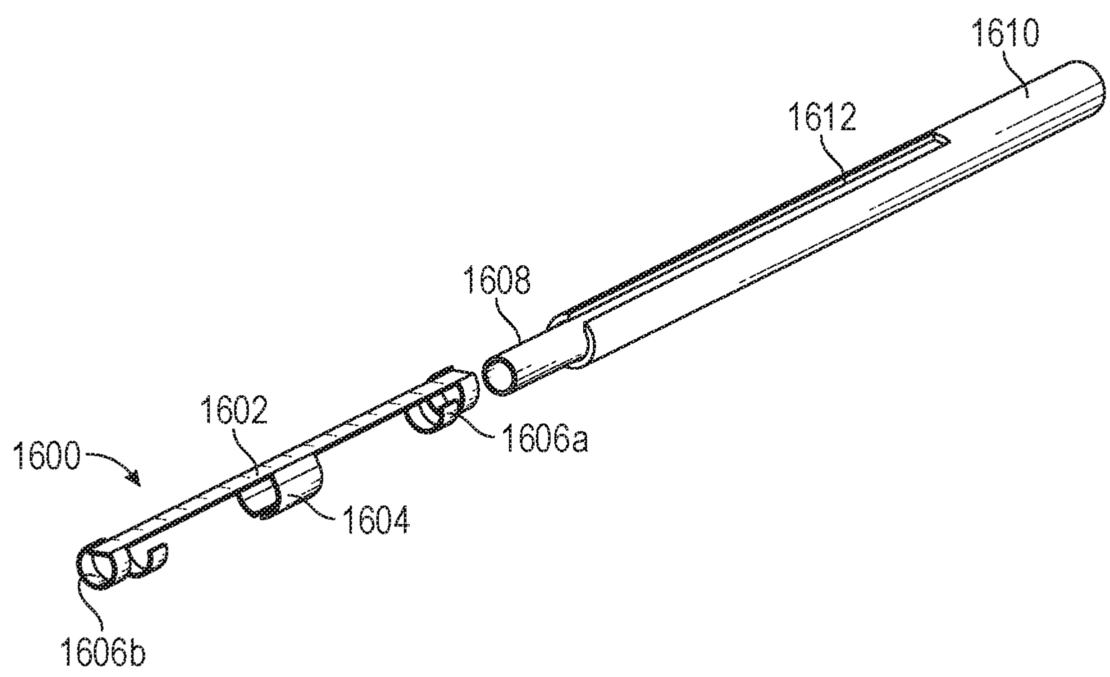
FIGS. 16A and 16B illustrate coupling of an anchor spine to a shaping catheter in accordance with the principles of the present disclosure.
Figure 16B:
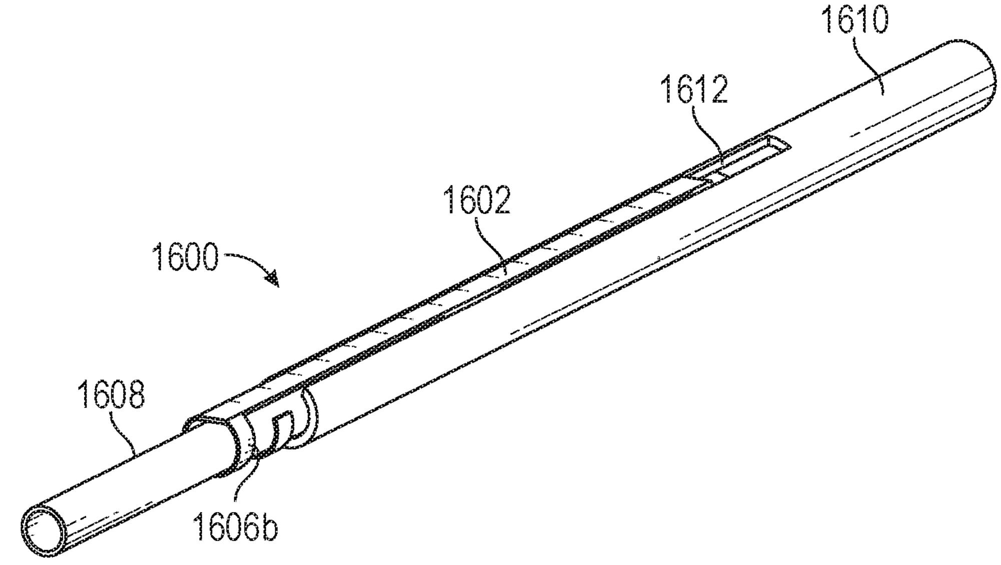

Referring now to FIGS. 16A and 16B, an exemplary coupling of an anchor spine to the support is provided. As described above, anchor 110 may be coupled to support 200 to anchor support 200 intraluminally, thereby anchoring prosthetic device 120 in a free-standing, suspended manner in the native heart valve. As described in U.S. Pat. No. 11,219,525 to Vesely, the entire contents of which are incorporated herein by reference, the anchor may include an anchor spine that may be coupled to the support, e.g., via an anchor tube slidably disposed over the support. As described herein with regard to FIGS. 16A and 16B, anchor connector 1600 may include anchor spine 1602, which may be directly coupled to the support, e.g., second shaping catheter 1608, without the need for an anchor tube. Alternatively, anchor spine 1602 may be coupled to an anchor tube slidably disposed over second shaping catheter 1608.

As shown in FIG. 16A, anchor spine 1602, which is coupled to a stent (not shown), may include central guiding portion 1604 having a passageway sized and shaped to receive second shaping catheter 1608 therethrough. Central guiding portion 1604 may be aligned with anchor spine 1602 to centralize the support relative to the stent. In addition, anchor spine 1602 may include one or more flexible guiding portions, e.g., proximal flexible guiding portions 1606*a* disposed proximal to central guiding portion 1604 and distal flexible guiding portions 1606*b* disposed distal to central guiding portion 1604. The flexible guiding portions are configured to transition between a radially collapsed state and an radially expanded state, and are biased toward the radially collapsed state. Accordingly, the flexible guiding portions may be transitioned to the radially expanded state upon an application of force thereon. Moreover, in the radially expanded state, the axes of the passageways of the flexible guiding portions are aligned with the axis of the passageway of central guiding portion 1604, and are sized and shaped to receive second shaping catheter 1608 therethrough.

As shown in FIGS. 16A and 16B, a temporary catheter, e.g., stent support catheter 1610, may be used to facilitate coupling of anchor spine 1602 and second shaping catheter 1608. For example, stent support catheter 1610 may have a lumen sized and shaped to receive second shaping catheter 1608, central guiding portion 1604, and the flexible guiding portions in their radially expanded states therethrough. In addition, stent support catheter 1610 may have opening 1612 sized and shaped to receive anchor spine 1602 therein. For example, opening 1612 may have a geometry that corresponds with the geometry of stent support catheter 1610, such that when central guiding portion 1604 and the flexible guiding portions are disposed within the lumen of stent support catheter 1610, opening 1612 limits or prevents rotation of anchor spine 1602 relative to stent support catheter 1610, while permitting stent support catheter 1610 to slide axially over an entire length of anchor spine 1602, thereby providing rigidity to central guiding portion 1604 and the flexible guiding portions.

To couple anchor spine 1602 to second shaping catheter 1608, the flexible guiding portions may be expanded to their expanded states such that the flexible guiding portions and central guiding portion 1604 may be disposed within the lumen of stent support catheter 1610. The inner surface of stent support catheter 1610 applies a force to the flexible guiding portions disposed therein to maintain the flexible guiding portions in their expanded states. Accordingly, second shaping catheter 1608 may be advanced through proximal flexible guiding portions 1606*a*, central guiding portion 1604, and distal flexible guiding portions 1606*b*, until anchor spine 1602 is in a desired position along second shaping catheter 1608. Stent support catheter 1610 may then be removed, thereby removing the force applied to the flexible guiding portions, such that the flexible guiding portions transition toward their collapsed states. Accordingly, the flexible guiding portions will clamp onto second shaping catheter 1608 to thereby lock anchor spine 1602 relative to second shaping catheter 1608.

During the removal of stent support catheter 1610, the retention force between second shaping catheter 1608 and anchor spine 1602 may be increased by applying a biocompatible elastomer on the outer surface of second shaping catheter 1608. Moreover, although four proximal flexible guiding portions are illustrated in FIG. 16A, as will be understood by a person having ordinary skill in the art, less or more than four proximal flexible guiding portions may be coupled to anchor spine 1602 to decrease or increase the retention force between second shaping catheter 1608 and anchor spine 1602.

Alternatively, the outer surface of shaping catheter may include a number of grooves corresponding to the number of flexible guiding portions, such that the grooves are sized and shaped to receive the flexible guiding portions therein. For example, the grooves may have a geometry corresponding to the geometry of the flexible guiding portions, such that when the flexible guiding portions are disposed within the grooves, axial and rotational movement of the anchor spine relative to the shaping catheter is limited or prevented. In this embodiment, to couple the anchor spine to the shaping catheter, a stent support catheter may be disposed between the shaping catheter and the flexible guiding portions in their expanded state. For example, the flexible guiding portions may be expanded to their expanded state, and the stent support catheter may be inserted through the flexible guiding portions to thereby maintain the flexible guiding portions in their expanded state. The shaping catheter may then be inserted through the lumen of the stent support catheter until the flexible guiding portions are aligned with the grooves on the outer surface of the shaping catheter. Accordingly, upon removal of the stent support catheter, the flexible guiding portions will transition toward their collapsed states within the corresponding grooves to thereby limit or prevent axial and rotational movement of the anchor spine relative to the shaping catheter.

In some embodiments, the flexible guiding portions may be one or more compliant rings, such that a stent support catheter may be inserted through the compliant rings to expand the compliant rings to an expanded state, and the shaping catheter may be inserted through the lumen of the stent support catheter until the anchor spine is in a desired position relative to the shaping catheter. Upon removal of the stent support catheter, the compliant rings will transition toward their collapsed states and clamp the shaping catheter to thereby prevent axial and rotational movement of the anchor spine relative to the shaping catheter. As will be understood by a person having ordinary skill in the art, when only one shaping catheter is utilized, e.g., when the support only has one adjustable bend, the anchor spines described herein may be directly coupled to the corresponding shaping catheter or the outermost catheter of the support.

Referring now to FIGS. 17A to 17B, an exemplary mechanism for adjusting the position of the one or more adjustable bends of the heart valve therapeutic device is provided. As described in U.S. Pat. No. 11,219,525 to Vesely, the entire contents of which are incorporated herein by reference, the anchor may be coupled to the support via an anchor tube slidably disposed over the support. For example, as shown in FIGS. 17A and 17B, anchor tube 1700 coupled to a stent (not shown) may be slidably disposed over at least the proximal region of the distal, implantable portion of the support, e.g., second shaping catheter 1710. As anchor tube 1700 is implanted within a vessel coupled to the patient's heart, second shaping catheter 1710 may be moved axially relative to anchor tube 1700 to thereby adjust the position of the one or more adjustable bends of the support relative to the patient's native heart valve.

As shown in FIG. 17B, at least a proximal portion of the outer surface of second shaping catheter 1710 may have a threaded surface. Moreover, driver 1704 may be rotatably disposed within the lumen of anchor tube 1700. For example, the proximal end of driver 1708 may include one or more grooves 1708 sized and shaped to engage with a rotation member, such that the rotation member may be engaged with groove 1708 and rotated to thereby cause rotation of driver 1704 relative to anchor tube 1700. Shoulder portion 1706 of driver 1704 may have an outer diameter larger than the proximal portion of driver 1704, and may have a lumen sized and shaped to receive the proximal portion of second shaping catheter 1710 therein. In addition, the inner surface of shoulder portion 1706 of driver 1704 may have a threaded surface configured to rotatably engage with the threaded surface on the outer surface of second shaping catheter 1710. Driver 1704 is axially controlled relative to anchor tube 1700 and second shaping catheter 1710 is rotationally fixed relative to anchor tube 1700, such that rotation of driver 1704 causes translational movement of second shaping catheter 1710 relative to driver 1704 and anchor tube 1700.

Anchor tube 1700 may include a control mechanism for controlling/limiting axial movement of driver 1704 relative to anchor tube 1700, e.g., one or more pins, tabs, flaps, etc. For example, as shown in FIG. 17B, anchor tube 1700 may have one or more pairs of inward facing tabs or flaps, e.g., flaps 1702*a* and 1702*b*, configured to control/limit axial movement of driver 1704 relative to anchor tube 1700. For example, flap 1702*a* may be positioned on a proximal side of shoulder portion 1706 and flap 1704*b* may be positioned on a distal side of shoulder portion 1706, such that driver 1704 may rotate within anchor tube 1700, but axial movement of driver 1704 is controlled or otherwise limited relative to anchor tube 1700. Moreover, second shaping catheter 1710 may include rail 1714 extending along at least a portion of the proximal portion of second shaping catheter 1710, such that rail 1714 is sized and shaped to slidably receive inward facing tab or flap of anchor tube 1700, e.g., tab 1702*c*. Rail 1714 permits tab 1702*c* to move axially along rail 1714, while preventing rotation of second shaping catheter 1710 relative to anchor tube 1700.

Referring now to FIG. 17C, an alternative exemplary mechanism for adjusting the position of the one or more adjustable bends of the heart valve therapeutic device is provided. As shown in FIG. 17C, the proximal end of anchor tube 1750 may include insert 1714 having lip portion 1716, such that the distal end of anchor tube 1750 and lip portion 1716 define groove 1718 extending circumferentially within the inner surface of anchor tube 1750 and insert 1714. Groove 1718 is sized and shaped to receive shoulder portion 1706 of driver 1704 therein, to thereby control or limit axial movement of driver 1704 relative to anchor tube 1750. Accordingly, as driver 1704 is rotated within groove 1718, the distal end of anchor tube 1700 and lip portion 1716 controls or limits axial movement of driver 1704 relative to anchor tube 1750, to thereby cause axial movement of second shaping catheter 1710 relative to anchor tube 1750.

Thus, in this embodiment, anchor tube 1750 also may include a control mechanism for controlling/limiting axial movement of driver 1704 relative to anchor tube 1750, e.g., one or more pins, tabs, flaps, etc. For example, second shaping catheter 1710 also may include a rail sized and shaped to slidably receive an inward facing tab or flap of anchor tube 1750, such that axial movement of second shaping catheter 1710 is permitted while rotational movement of second shaping catheter 1710 relative to the anchor tube is prevented. In some embodiments, insert 1714 and anchor tube 1750 may be formed as a single integrated component, such that groove 1718 is formed circumferentially along an inner surface of the anchor tube. As will be understood by a person having ordinary skill in the art, when only one shaping catheter is utilized, e.g., when the support only has one adjustable bend, the anchor tubes described herein may be slidably disposed over the corresponding shaping catheter or the outermost catheter of the support.

Figure 18A:
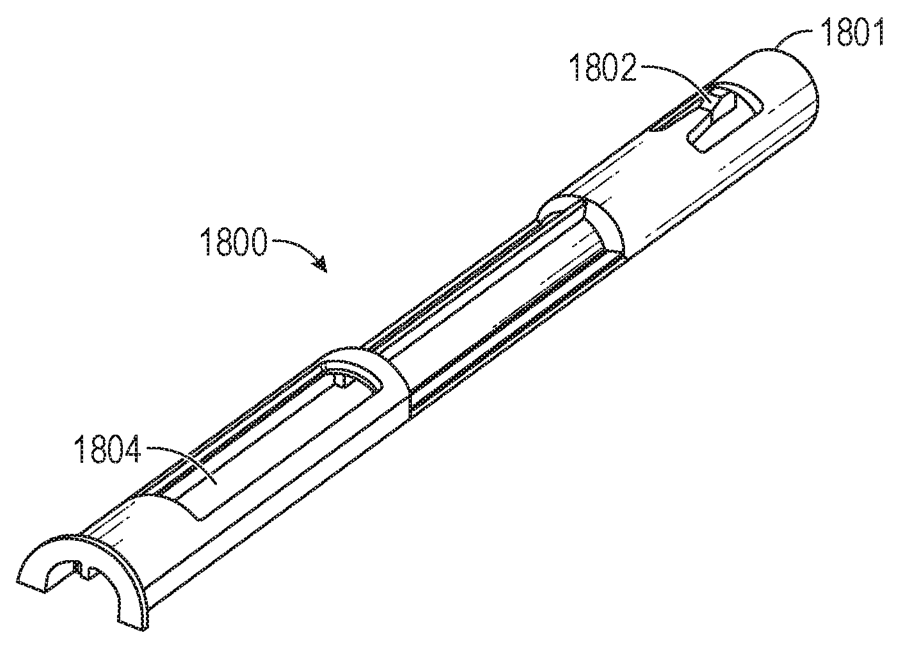
FIGS. 18A to 18C illustrate an exemplary mechanism for limiting adjustment of the axial location of the one or more adjustable bends of the heart valve therapeutic device constructed in accordance with the principles of the present disclosure.
Figure 18B:
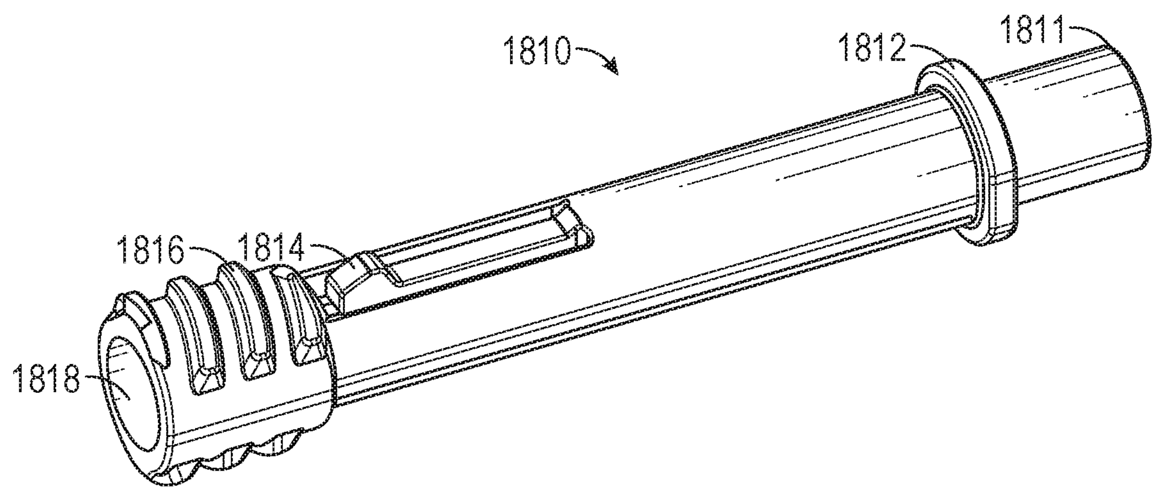
Figure 18C:
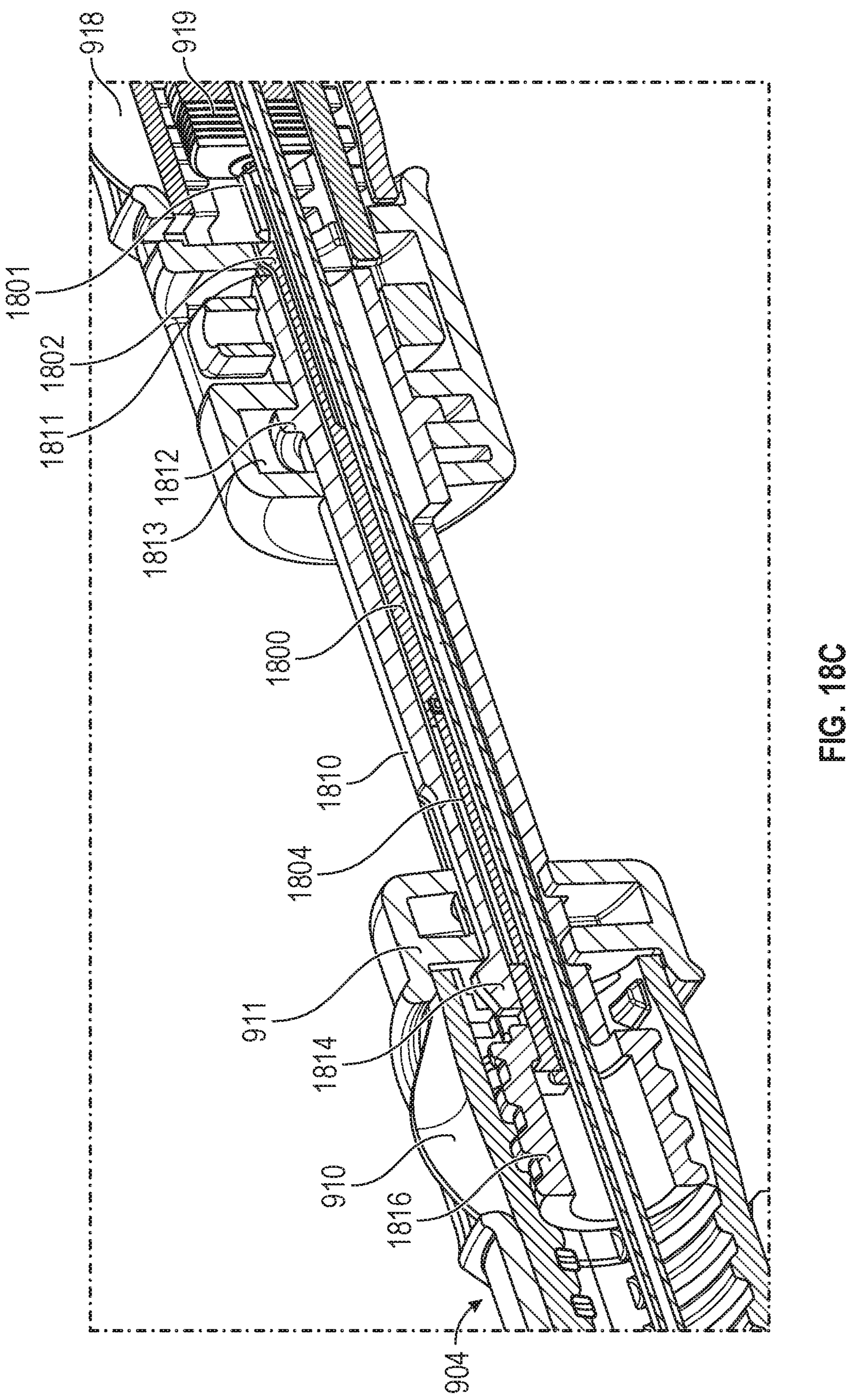

Referring now to FIGS. 18A to 18C, an exemplary mechanism for limiting adjustment of the axial location of the one or more adjustable bends of the heart valve therapeutic device is provided. As described above, proximal portion 902 of handle 900 may be rotatably coupled to distal portion 904, e.g., via a rod. Moreover, interface 910 of actuator 900 may be actuated to adjust the length of support 200, e.g., by adjusting the distance between proximal portion 902 and distal portion 904 along the rod, to thereby adjust the axial location of the one or more adjustable bends of elongated rail 206 relative to actuator 900. In addition, interface 918 may be operatively coupled to support 200 and actuated to lock the distal, implantable portion of support 200 to each other.

As described herein with regard to FIGS. 18A to 18C, handle 900 further may include axial control mechanism 1800, e.g., a slider component, configured to prevent a predefined additional amount of axial movement of proximal portion 902 relative to distal portion 904 until interface 918 has been fully actuated to lock the distal, implantable portion of support 200. As shown in FIG. 18A, axial control mechanism 1800 may include proximal end 1801, retention clip 1802, and opening 1804 distal to retention clip 1802. Retention clip 1802 may have a protrusion extending therefrom and is configured to be collapsed radially inward upon application of a force thereon, e.g., an axial force. Accordingly, a distal side of the protrusion of retention clip 1802 may be tapered to facilitate collapsing of retention clip 1802 upon application of an axial force thereon. Opening 1804 is sized and shaped to receive the safety clip of rod 1810 as described in further detail below.

As shown in FIG. 18B, rod 1810 may be configured to rotatably couple proximal portion 902 and distal portion 904, as well as to permit relative axial movement between proximal portion 902 and distal portion 904. Rod 1810 may include proximal end 1811, ridge 1812, safety clip 1814, threaded portion 1816, and lumen 1818. Ridge 1812 may extend at least partially circumferentially around an outer surface of rod 1810 to thereby fix rod 1810 axially relative to proximal portion 902 as described in further detail below. Safety clip 1814 may have a protrusion extending therefrom and is configured to be collapsed radially inward upon application of a force thereon, e.g., an axial force. Accordingly, a proximal side of the protrusion of safety clip 1814 may be tapered to facilitate collapsing of safety clip 1814 upon application of an axial force thereon. Moreover, safety clip 1814 is sized and shaped to be received through opening 1804 of axial control mechanism 1800. Threaded surface 1816 is configured to rotatably engage with interface 910, such that actuation of interface 910 may cause axial movement of distal portion 904 relative to rod 1810. In addition, lumen 1818 is sized and shaped to slidably receive axial control mechanism 1800 therein.

As shown in FIG. 18C, a proximal portion of rod 1810 may be disposed within proximal portion 902 of handle 900, such that ridge 1812 is disposed within groove 1813 of proximal portion 902, to thereby axially fix rod 1810 relative to proximal portion 902. In addition, a distal portion of rod 1810 may be disposed within distal portion 904 of handle 900, such that threaded surface 1816 is rotatably engaged with interface 910 and safety clip 1814 is adjacent to and/or abuts ridge 911 of the housing of distal portion 904. As shown in FIG. 18C, axial control mechanism 1800 may be disposed within the lumen of rod 1810, such that proximal end 1801 is disposed in proximity of driver 919 operatively coupled to interface 918. Axial control mechanism 1800 is slidably moveable within rod 1810, e.g., via an axial force applied by driver 919 upon actuation of interface 918, between a first position where retention clip 1802 is adjacent to and/or abuts proximal end 1811 of rod 1810 and opening 1804 is proximal to safety clip 1814 such that safety clip 1814 cannot collapse radially inward within opening 1804, and a second position where an axial force of proximal end 1811 of rod 1810 causes retention clip 1802 to collapse radially inward and opening 1804 is aligned with safety clip 1814 such that safety clip 1814 may collapse radially inward within opening 1804.

As described above, interface 910 may be actuated to cause axial movement of proximal portion 902 relative to distal portion 904 until ridge 911 abuts safety clip 1814. When axial control mechanism 1800 is in the first position, additional axial movement between proximal portion 902 and distal portion 904 is not permitted as safety clip 1814 cannot collapse radially inward due to an axial force applied by ridge 911, and thus safety clip 1814 prevents distal movement of distal portion 904 relative to rod 1810. Moreover, retention clip 1802 prevents axial movement of axial control mechanism 1800 relative to rod 1810. As described above, interface 918 may be actuated to lock the distal, implantable portion of support 200. As interface 918 is actuated, e.g., rotated, driver 919 operatively coupled thereto moves axially relative to interface 918. Accordingly, interface 918 may be required to be fully actuated, e.g., to fully lock the distal, implantable portion of support 200, before additional axial movement between proximal portion 902 and distal portion 904 is permitted.

For example, when interface 918 is fully actuated, driver 919 moves distally relative to interface 918, thereby abutting and applying an axial force on proximal end 1801 to cause distal movement of axial control mechanism 1800 relative to rod 1810. As axial control mechanism 1800 moves distally relative to rod 1810, proximal end 1811 of rod 1810 applies an axial force on retention clip 1802 to thereby radially collapse retention clip 1802 inward. Axial control mechanism 1800 may continue to move distally until interface 918 is fully actuated, and opening 1804 is aligned with safety clip 1814 in the second position. Accordingly, upon full actuation of interface 918, such that the distal, implantable portion of support 200 is fully locked, interface 910 may then be further actuated to provide a predefined additional amount of axial movement of proximal portion 902 relative to distal portion 904. Specifically, further actuation of interface 910 will cause ridge 911 to apply an axial force to safety clip 1814, e.g., as proximal portion 902 moves proximally relative to distal portion 904, such that safety clip 1814 collapses radially inward within opening 1804.

Figures 19, 20:
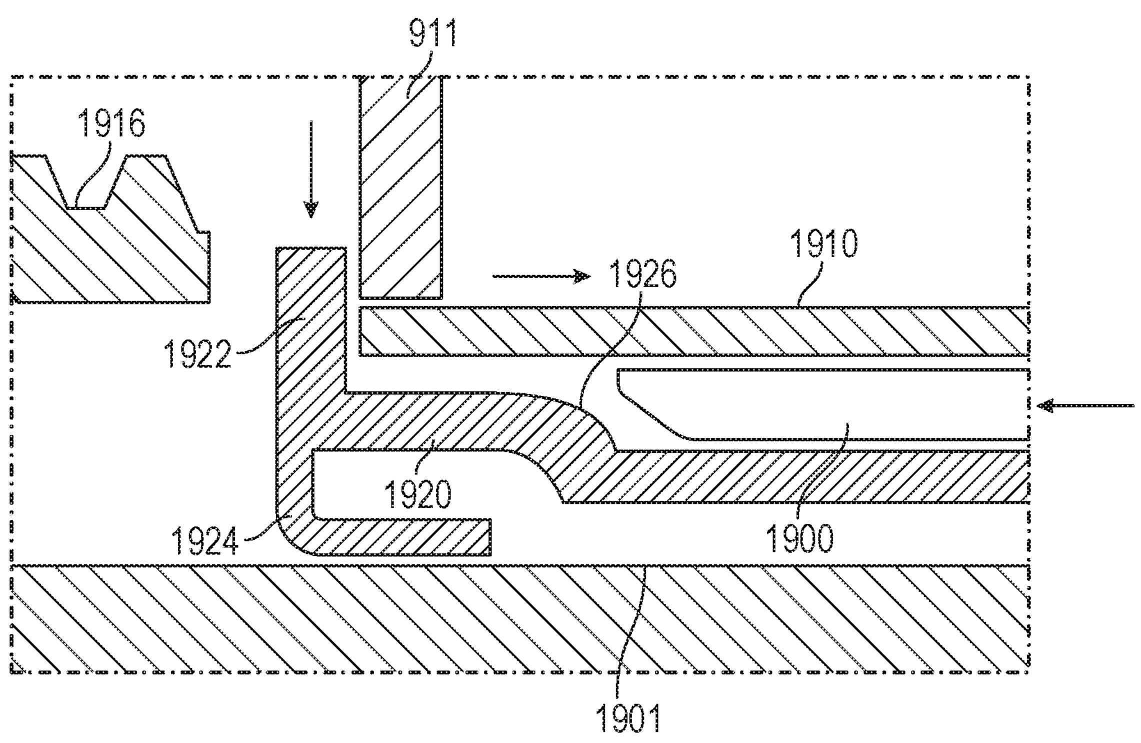
FIG. 19 illustrates an alternative exemplary mechanism for limiting adjustment of the axial location of the one or more adjustable bends of the heart valve therapeutic device constructed in accordance with the principles of the present disclosure.
FIG. 20 illustrates another alternative exemplary mechanism for limiting adjustment of the axial location of the one or more adjustable bends of the heart valve therapeutic device constructed in accordance with the principles of the present disclosure.

Referring now to FIG. 19, another exemplary mechanism for limiting adjustment of the axial location of the one or more adjustable bends of the heart valve therapeutic device is provided. As shown in FIG. 19, rod 1910 may include guide rail 1901 disposed therein having a lumen configured to slidably receive the proximal, delivery portion of support 200 therethrough. Moreover, the proximal and distal portions of the handle may be rotatably coupled to each other via rod 1910. Rod 1910 includes threaded surface 1916 rotatably coupled to interface 910, such that actuation of interface 910 causes relative axial movement between the proximal and distal portions of the handle along rod 1910. In addition, rod 1910 may be axially fixed relative to proximal portion 902.

As shown in FIG. 19, the axial control mechanism may include slider component 1900 and interlock component 1920. Interlock component 1920 may be at least partially disposed within slider component 1900, and slider component 1900 may be slidably disposed between interlock component 1920 and rod 1910. Interlock component 1920 may be axially fixed relative to rod 1910, and may be configured to collapse radially inward due to an application of force, e.g., an axial force. For example, interlock component 1920 may include upper portion 1922, hinge portion 1926, and optional spring portion 1924. Spring portion 1924 may contact guide rail 1901 to keep upper portion 1922 adjacent to ridge 911. Moreover, slider component 1900 may be slidably moveable between a first position where slider component does not interact with interlock component 1920, and upper portion 1922 is adjacent to or abuts ridge 911 of the housing of distal portion 904, and a second position where slider component 1900 applies an axial force to hinge portion 1926 thereby causing spring portion 1924 to contact guide rail 1901, such that guide rail 1910 causes spring portion 1924 to collapse/compress and interlock component 1920 collapses radially inward such that upper portion 1922 is no longer adjacent to ridge 911. In some embodiments, interlock component 1920 does not include spring portion 1924, such that hinge portion 1926 has sufficient force to maintain upper portion 1922 adjacent to ridge 911, and the axial force applied to hinge portion 1926 by slider component 1900 causes interlock component 1920 to collapse radially inward such that upper portion 1922 is no longer adjacent to ridge 911.

As described above, interface 918 may be required to be fully actuated, e.g., to fully lock the distal, implantable portion of support 200, before additional axial movement between the proximal and distal portions of the handle is permitted. For example, interface 910 may be actuated to cause axial movement of proximal portion 902 relative to distal portion 904 until ridge 911 abuts upper portion 1922. When slider component 1900 is in the first position, additional axial movement between proximal portion 902 and distal portion 904 is not permitted as upper portion 1922 prevents interlock component 1920 from collapsing radially inward due to an axial force applied by ridge 911, and thus upper portion 1922 prevents distal movement of distal portion 904 relative to rod 1910. As described above, as interface 918 is actuated, e.g., rotated, driver 919 operatively coupled thereto moves axially relative to interface 918. Accordingly, interface 918 may be required to be fully actuated, e.g., to fully lock the distal, implantable portion of support 200, before additional axial movement between proximal portion 902 and distal portion 904 is permitted.

For example, when interface 918 is fully actuated, driver 919 moves distally relative to interface 918, thereby abutting and applying an axial force on proximal end of slider component 1900 to cause distal movement of slider component 1900 relative to rod 1910. Slider component 1900 may continue to move distally relative to rod 1910 until interface 918 is fully actuated and the distal end of slider component 1900 abuts and applies an axial force to hinge portion 1926 to thereby collapse interlock component 1920 radially inward, such that upper portion 1922 disengages with ridge 911. Accordingly, upon full actuation of interface 918, such that the distal, implantable portion of support 200 is fully locked, interface 910 may then be further actuated to provide a predefined additional amount of axial movement of proximal portion 902 relative to distal portion 904. Specifically, further actuation of interface 910 will be permitted as upper portion 1922 will no longer prevent proximal movement of interlock component 1920 and rod 1910, and accordingly proximal portion 902, relative to ridge 911 and distal portion 904. Like axial control mechanism 1800, slider component 1900 also may include a retention clip mechanism configured to prevent distal movement of slider component 1900 relative to rod 1910 without application of an axial force thereon, e.g., via a driver operatively coupled to interface 918.

Referring now to FIG. 20, another exemplary mechanism for limiting adjustment of the axial location of the one or more adjustable bends of the heart valve therapeutic device is provided. As shown in FIG. 20, the proximal and distal portions of the handle may be rotatably coupled to each other via rod 2010. Rod 2010 may include safety clip 2012 configured to be collapsed sideways within rod 2010 upon application of a force thereon, e.g., an axial force. For example, a proximal surface of safety clip 2012 may be tapered to facilitate collapse of safety clip 2012 upon application of an axial force thereon. In addition, safety clip 2012 may include protrusion 2014 disposed thereon, such that protrusion 2014 prevents additional axial movement of proximal portion 902 relative to distal portion 904. For example, interface 910 may be actuated to cause axial movement of proximal portion 902 relative to distal portion 904 until ridge 911 abuts protrusion 2014.

As shown in FIG. 20, axial control mechanism 2000, e.g., a slider component, may be slidably disposed within rod 2010. Axial control mechanism 2000 may be slidably moveable between a first position when axial control mechanism 2000 does not interact with safety clip 2012, and a second position where axial control mechanism 2000 applies an axial force to safety clip 2012, thereby causing safety clip 2012 to collapse sideways, such that protrusion 2014 is aligned with opening 913 of ridge 911. As described above, interface 918 may be required to be fully actuated, e.g., to fully lock the distal, implantable portion of support 200, before additional axial movement between proximal portion 902 and distal portion 904 is permitted.

For example, when interface 918 is fully actuated, driver 919 moves distally relative to interface 918, thereby abutting and applying an axial force on proximal end of axial control mechanism 2000 to cause distal movement of axial control mechanism 2000 relative to rod 2010. Axial control mechanism 2000 may continue to move distally relative to rod 2010 until interface 918 is fully actuated and the distal end of axial control mechanism 2000 abuts and applies an axial force to safety clip 2012 to thereby collapse safety clip 2012 sideways, e.g., in a lateral direction relative to the direction of the axial force by axial control mechanism 2000, such that protrusion 2014 is aligned with opening 913 of ridge 911 of the housing of distal portion 904. Accordingly, upon full actuation of interface 918, such that the distal, implantable portion of support 200 is fully locked, interface 910 may then be further actuated to provide a predefined additional amount of axial movement of proximal portion 902 relative to distal portion 904. Specifically, further actuation of interface 910 will be permitted as protrusion 2014 is aligned with opening 913, and thus ridge 911 may move proximally relative to rod 2010 as protrusion 2014 passes through opening 913. Like axial control mechanism 1800, axial control mechanism 2000 also may include a retention clip mechanism configured to prevent distal movement of axial control mechanism 2000 relative to rod 2010 without application of an axial force thereon, e.g., via a driver operatively coupled to interface 918.

Referring now to FIGS. 21A to 21C, an exemplary actuator interlocking mechanism constructed in accordance with the principles of the present disclosure. Actuation of an actuator of handle 900, e.g., any of the interfaces described herein, may be locked until another corresponding interface is fully actuated. For example, interface 910 may be locked until interface 918 is fully actuated, such that interface 910 may not be actuated until interface 918 is fully actuated. As shown in FIG. 21A, interface 910 may include opening 2104 and ridge 911 of the housing of distal portion 904 may include opening 2106, such that openings 2104 and 2106 are sized and shaped to slidably receive pin 2102 therein. For example, openings 2104 and 2106 may have a geometry corresponding to the geometry of pin 2102 such that when pin 2102 is disposed within at least a portion of both openings 2104 and 2106, pin 2102 prevents rotational movement of interface 910 relative to ridge 911. Moreover, the friction forces between pin 2102 and openings 2104 and 2106 prevent pin 2102 from inadvertently disengaging with openings 2104 and 2106, such that pin 2102 is only removably from openings 2104 and 2106 via the axial force applied by axial control mechanism 2100. Accordingly, while pin is disposed within openings 2104 and 2106, interface 910 is locked relative to ridge 911 and thus cannot be actuated. As shown in FIG. 21B, interface 910 may include more than one opening for slidably receiving more than one pin.

Referring again to FIG. 21A, handle 900 may include axial control mechanism 2100 slidably disposed within rod 2110. Axial control mechanism 2100 may be slidably moveable between a first portion when axial control mechanism 2100 does not engage with pin 2102, and a second position where axial control mechanism 2100 applies an axial force to pin 2102, thereby causing pin 2102 to move further into opening 2104 of interface 910 and out of opening 2106 of ridge 911, as shown in FIG. 21C. Once pin 2102 is no longer disposed within opening 2106 of ridge 911, interface 910 may be freely actuated and rotate relative to ridge 911. Accordingly, interface 918 may be required to be fully actuated, e.g., to fully lock the distal, implantable portion of support 200, before actuation of interface 910 is permitted.

For example, when interface 918 is fully actuated, driver 919 moves distally relative to interface 918, thereby abutting and applying an axial force on proximal end of axial control mechanism 2100 to cause distal movement of axial control mechanism 2100 relative to rod 2110. Axial control mechanism 2100 may continue to move distally relative to rod 2110 until interface 918 is fully actuated and the distal end of axial control mechanism 2100 abuts and applies an axial force to pin 2102 to thereby push pin 2102 further into opening 2104 of interface 910 and out of opening 2106 of ridge 911. Accordingly, upon full actuation of interface 918, such that the distal, implantable portion of support 200 is fully locked, interface 910 may then be actuated to provide axial movement of proximal portion 902 relative to distal portion 904. As will be understood by a person having ordinary skill in the art, the actuator locking mechanism described with regard to FIGS. 21A to 21C may be implemented in other interfaces of handle 900.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for implanting a therapeutic heart valve device at a native heart valve of a patient's heart, the system comprising:

- a prosthetic device configured to be implanted at the native heart valve; and
- a support configured to maintain the prosthetic device at the native heart valve, the support comprising:
  - a first adjustable bend comprising a preformed bend and configured to be actuated to adjust a position of the prosthetic device along a first plane; and
  - a second adjustable bend proximal to the first adjustable bend, the second adjustable bend configured to be actuated to adjust the position of the prosthetic device along a second plane,
- wherein an orientation of the first plane is dependent on the position of the prosthetic device along the second plane.

2. The system of claim 1, wherein the first and second adjustable bends are configured to be actuated to adjust the position of the prosthetic device along the first and second planes to facilitate navigation of the prosthetic device through the patient's inferior vena cava (IVC) and right atrium to the patient's tricuspid valve.

3. The system of claim 1, wherein the support comprises:

- an elongated rail extending concentrically through and configured to be coupled to the prosthetic device, the elongated rail comprising the preformed bend and having a first flexibility;
- a first shaping catheter slidably disposed over the elongated rail such that movement of the first shaping catheter over the preformed bend of the elongated rail adjusts an angle of the first adjustable bend, the first shaping catheter having a second flexibility less flexible than the first flexibility.

4. The system of claim 3, wherein the first shaping catheter comprises a distal portion having a first stiffness and a proximal portion having a second stiffness more stiff than the first stiffness, such that movement of the distal portion of the first shaping catheter over the preformed bend does not adjust the angle of the first adjustable bend, whereas movement of the proximal portion of the first shaping catheter over the preformed bend adjusts the angle of the first adjustable bend, thereby minimizing damage to the support.

5. The system of claim 3, wherein the elongated rail comprises the second adjustable bend having a second preformed bend, and wherein the support further comprises a second shaping catheter slidably disposed over the first shaping catheter such that movement of the second shaping catheter over the second preformed bend of the elongated rail adjusts an angle of the second adjustable bend, the second bend shaping catheter having a third flexibility less flexible than the second flexibility.

6. The system of claim 5, wherein the second shaping catheter comprises a distal portion having a first stiffness and a proximal portion having a second stiffness more stiff than the first stiffness, such that movement of the distal portion of the second shaping catheter over the second preformed bend does not adjust the angle of the second adjustable bend, whereas movement of the proximal portion of the second shaping catheter over the second preformed bend adjusts the angle of the second adjustable bend, thereby minimizing damage to the support.

7. The system of claim 5, wherein the support comprises a valve support catheter slidably disposed over the second shaping catheter and coupled to the prosthetic device, the valve support catheter having a fourth flexibility more flexible than the first flexibility, such that movement of the valve support catheter relative to the native heart valve adjusts a depth of the prosthetic device relative to the native heart valve without adjusting, or minimally adjusting, the position of the first and second adjustable bends.

8. The system of claim 5, wherein the elongated rail comprises an elongated rail distal portion extending concentrically through and coupled to the prosthetic device and an elongated rail proximal portion, the elongated rail distal portion configured to be attached to the elongated rail proximal portion during delivery of the prosthetic device, and detached from the elongated rail proximal portion for implantation of the elongated rail distal portion and the prosthetic device.

9. The system of claim 8, wherein the first shaping catheter comprises a first shaping catheter distal portion and a first shaping catheter proximal portion, the first shaping catheter distal portion configured to be attached to the first shaping catheter proximal portion during delivery of the prosthetic device, and detached from the first shaping catheter proximal portion for implantation of the first shaping catheter distal portion.

10. The system of claim 9, wherein the first shaping catheter distal portion comprises a lock configured to lock the first shaping catheter distal portion to the elongated rail distal portion.

11. The system of claim 10, wherein the second shaping catheter comprises a second shaping catheter distal portion and a second shaping catheter proximal portion, the second shaping catheter distal portion configured to be attached to the second shaping catheter proximal portion during delivery of the prosthetic device, and detached from the second shaping catheter proximal portion for implantation of the second shaping catheter distal portion.

12. The system of claim 11, wherein the second shaping catheter distal portion comprises a lock configured to lock the second shaping catheter distal portion to the first shaping catheter distal portion.

13. The system of claim 1, wherein the prosthetic device comprises a spine configured to be coupled to a distal region of the support via a spine connector.

14. The system of claim 13, wherein the spine connector comprises a plurality of ridges disposed at a proximal region of the spine, and wherein the support is configured to expand responsive to an external stimulus, such that the distal region of the support is configured to be disposed over the plurality of ridges in an expanded state and coupled to the proximal region of the spine via an interference fit between an inner surface of the distal region of the support and the plurality of ridges upon removal of the external stimulus.

15. The system of claim 13, wherein the spine connector comprises an elongated rod having a proximal end coupled to the distal region of the support and a distal end comprising one or more collapsible prongs, the one or more collapsible prongs comprising a protrusion, and wherein a distal region of the spine comprises one or more grooves configured to receive the protrusion when the one or more collapsible prongs are in an expanded state, such that the spine is configured to be disposed over the distal end of the spine connector when the one or more collapsible prongs are in a collapsed state until a proximal end of the spine abuts an abutment disposed at the distal region of the support and the protrusion engages the one or more grooves in the expanded state, thereby preventing axial and rotational movement between the spine and the spine connector.

16. The system of claim 13, wherein the spine connector comprises an elongated rod having a proximal end coupled to the distal region of the support and a distal end configured to be coupled to a plug having a distal abutment, such that the spine is configured to be disposed over the distal end of the spine connector until a proximal end of the spine abuts a proximal abutment disposed at the distal region of the support, and wherein the plug is configured to be coupled to the distal end of the elongated rod, such that the proximal and distal abutments prevent relative axial and rotational movement between the spine and the spine connector.

17. The system of claim 1, further comprising a stent configured to anchor the support to a blood vessel coupled to the heart.

18. The system of claim 17, further comprising:

a stent tube slidably disposed over the support, a first portion of the stent tube pivotally coupled to a first portion of the stent, a second portion of the stent tube moveably coupled to a second portion of the stent such that movement of the second portion of the stent tube along the second portion of the stent causes the stent tube to pivot about the first portion of the stent to thereby adjust an angle of the second adjustable bend.

19. The system of claim 18, wherein the second portion of the stent comprises a rail such that the second portion of the stent tube is moveable along the rail.

20. The system of claim 17, further comprising:

a stent tube slidably disposed over the support, the stent tube comprising a first portion pivotally coupled to a first portion of the stent and a second portion configured to freely move relative to the stent such that the stent tube pivots about the first portion of the stent responsive to movement of the prosthetic device throughout multiple cardiac cycles.

21. The system of claim 17, further comprising:

a stent tube slidably disposed over the support, the stent tube comprising a first portion rigidly coupled to a first portion of the stent and a second portion rigidly coupled to a second portion of the stent such that the stent tube does not move relative to the stent throughout multiple cardiac cycles.

22. The system of claim 17, wherein the stent comprises a stent spine having one or more flexible guiding portions configured to transition between a radially collapsed state and a radially expanded state, the system further comprising:

a stent support catheter slidably disposed over the one or more flexible guiding portions in the radially expanded state, wherein the one or more flexible guiding portions are biased toward the radially collapsed state, such that the one or more flexible guiding portions are configured to receive the support therethrough in the radially expanded state within the stent support catheter, and upon removal of the stent support catheter, the one or more flexible guiding portions are configured to clamp the support.

23. The system of claim 22, wherein the stent spine comprises a central guiding portion configured to be slidably disposed within the stent support catheter, the central guiding portion configured to receive the support therethrough.

24. The system of claim 23, wherein the one or more flexible guiding portions comprise at least one of one or more proximal flexible guiding portions disposed on the stent spine proximal to the central guiding portion or one or more distal flexible guiding portions disposed on the stent spine distal to the central guiding portion.

25. The system of claim 17, wherein the stent comprises a stent spine having one or more flexible guiding portions configured to transition between a radially collapsed state and a radially expanded state, and wherein an outer surface of the support comprises one or more grooves configured to receive the one or more flexible guiding portions, the system further comprising:

a stent support catheter slidably disposable between the support and the one or more flexible guiding portions in the radially expanded state, wherein the one or more flexible guiding portions are biased toward the radially collapsed state, such that the stent support catheter is configured to maintain the one or more flexible guiding portions in the radially expanded state as the stent support catheter receives the support therein, and upon removal of the stent support catheter, the one or more flexible guiding portions are configured to transition to the radially collapsed state within the one or more grooves to thereby prevent axial movement between the stent spine and the support.

26. The system of claim 17, wherein the stent comprises a stent spine having one or more compliant rings, the system further comprising:

a stent support catheter configured to be received through and expand the one or more compliant rings to a radially expanded state, the stent support catheter configured to slidably receive the support therein, wherein, upon removal of the stent support catheter, the one or more compliant rings are configured to clamp the support.

27. The system of claim 17, wherein the stent comprises a stent tube slidably disposed over the support, and wherein an outer surface of a proximal region of the support comprises a first threaded surface, the system further comprising:

a rotatable driver disposed within the stent tube, the rotatable driver having a lumen sized and shaped to receive the proximal region of the support therein, an inner surface of the rotatable driver comprising a second threaded surface configured to rotatably engage with the first threaded surface of the proximal region of the support, wherein the rotatable driver is axially controlled relative to the stent tube and the support is rotationally fixed relative to the stent tube, such that rotation of the rotatable driver causes translational movement of the support relative to the stent tube via the first and second threaded surfaces.

28. The system of claim 27, wherein the rotatable driver comprises a shoulder portion, wherein the outer surface of the proximal region of the support comprises a rail portion, and wherein the stent tube comprises:

one or more pairs of inward facing flaps configured to lock the shoulder portion of the rotatable driver to axially control the rotatable driver relative to the stent tube; and one or more inward facing tabs configured to slidably engage with the rail portion to rotationally fix the support relative to the stent tube.

29. The system of claim 27, wherein the rotatable driver comprises a shoulder portion, and wherein an inner surface of the stent tube comprises a groove sized and shaped to receive the shoulder portion therein to thereby axially control the rotatable driver relative to the stent tube.

30. The system of claim 17, wherein the stent comprises an expandable wire frame having a proximal draping portion and distal draping portion, the distal draping portion comprising more flexibility than the proximal draping portion of the expandable wire frame.

31. The system of claim 30, wherein the expandable wire frame comprises strut rings each extending around a circumference of the stent, wherein the strut rings in the distal draping portion are thinner than the strut rings in the proximal draping portion.

* * * * *